United States Patent
Lin et al.

(10) Patent No.: US 8,501,925 B2
(45) Date of Patent: Aug. 6, 2013

(54) NUCLEIC ACID MODULES FOR EXPRESSION AND TAGGING OF MEMBRANE PROTEINS AND METHODS OF USE

(75) Inventors: Li Lin, Baltimore, MD (US); John Pang, Baltimore, MD (US); Wen Wei, Cockeysville, MD (US); Edward G. Lakatta, Bel Air, MD (US)

(73) Assignee: The United States of America, as represented by the Secretary, Department of Health and Human Resources, Washington, DC (US)

(*) Notice: Subject to any disclaimer, the term of this patent is extended or adjusted under 35 U.S.C. 154(b) by 644 days.

(21) Appl. No.: 12/652,395

(22) Filed: Jan. 5, 2010

(65) Prior Publication Data

US 2010/0173307 A1    Jul. 8, 2010

Related U.S. Application Data

(60) Provisional application No. 61/142,531, filed on Jan. 5, 2009.

(51) Int. Cl.
*C07H 21/04* (2006.01)
*C12Q 1/68* (2006.01)

(52) U.S. Cl.
USPC .......................................... 536/23.5; 435/6.1

(58) Field of Classification Search
None
See application file for complete search history.

(56) References Cited

U.S. PATENT DOCUMENTS

| 7,585,636 B2 | 9/2009 | Waldo et al. |
| 2005/0014251 A1* | 1/2005 | Sauer et al. ................ 435/320.1 |
| 2005/0221343 A1 | 10/2005 | Waldo et al. |

OTHER PUBLICATIONS https://tools.invitrogen.com/content/sfs/vectors/pcdna3.pdf, downloaded Sep. 2012.*
Cheng et al. Construction of different mutants of HA-tagged human Rage gene and their eukaryotic expression. Nan Fang Yi Ke Da Xue Xue Bao. Oct. 2008;28(10):1779-81. Chinese.*
Cheng et al. Construction of different mutants of HA-tagged human RAGE gene and their eukaryotic expression. Nan Fang Yi Ke Da Xue Xue Bao. Oct. 2008;28(10):1779-81. Translation.*
Cabantous et al., "Protein tagging and detection with engineered self-assembling fragments of green fluorescent protein," *Nature Biotechnology* 23(1):102-107, 2005.

* cited by examiner

*Primary Examiner* — Michele K Joike
(74) *Attorney, Agent, or Firm* — Klarquist Sparkman, LLP

(57) ABSTRACT

Described herein are nucleic acid modules for cloning, expression and tagging of eukaryotic membrane proteins. The nucleic acid modules include a receptor for advanced glycation end products (RAGE) signal sequence, a nucleic acid sequence encoding a tag and a multiple cloning sequence (MCS). Any membrane protein of interest can be cloned into the MCS for expression in cells. The nucleic acid modules can encode any type of tag, such as an epitope tag or affinity tag. The nucleic acid modules disclosed herein can be used to express any type of membrane protein and are particularly suited to the expression and tagging of Type I and Type III membrane proteins.

24 Claims, 11 Drawing Sheets

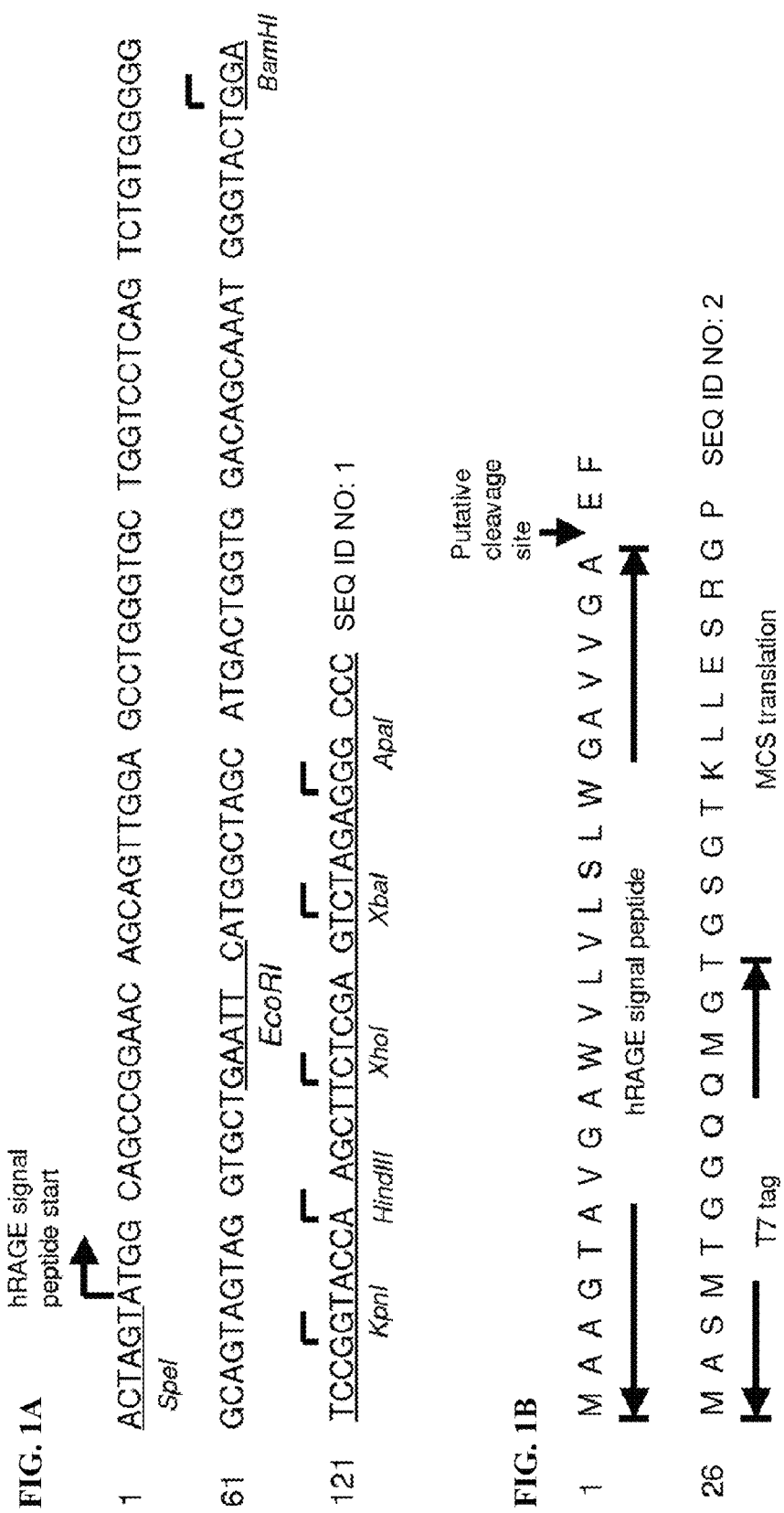

FIG. 1C

```
      hRAGE signal
      peptide start

1     ACTAGTATGG CAGCCGGAAC AGCAGTTGGA GCCTGGGGTGC TGGTCCTCAG TCTGTGGGGG
      ‾‾‾‾‾‾‾‾‾‾
      SpeI
61    GCAGTAGTAG GTGCTGAATT CGACTACAAA GATGACGATG ACAAGGGATC CGGTACCAAG
                             ‾‾‾‾‾‾               ‾‾‾‾‾‾‾‾‾‾‾          ‾‾‾‾‾‾‾‾‾‾
                             EcoRI                BamHI      KpnI      HindIII
121   CTTCTCGAGT CTAGAGGGCC C  SEQ ID NO: 3
      ‾‾‾‾‾‾‾‾‾‾ ‾‾‾‾‾ ‾‾‾‾
      XhoI       XbaI  ApaI
```

FIG. 1D

```
                                         Putative
                                         cleavage
                                         site
1     M A A G T A V G A W V L V L S L W G A V V G   A E F
      ←———————————————————————————————————————→    ↑
                  hRAGE signal peptide 26    D Y K D D D D K G S G T K L L E S R G P   SEQ ID NO: 4
      ↑                 ←————————————————→
      FLAG tag          MCS translation
```

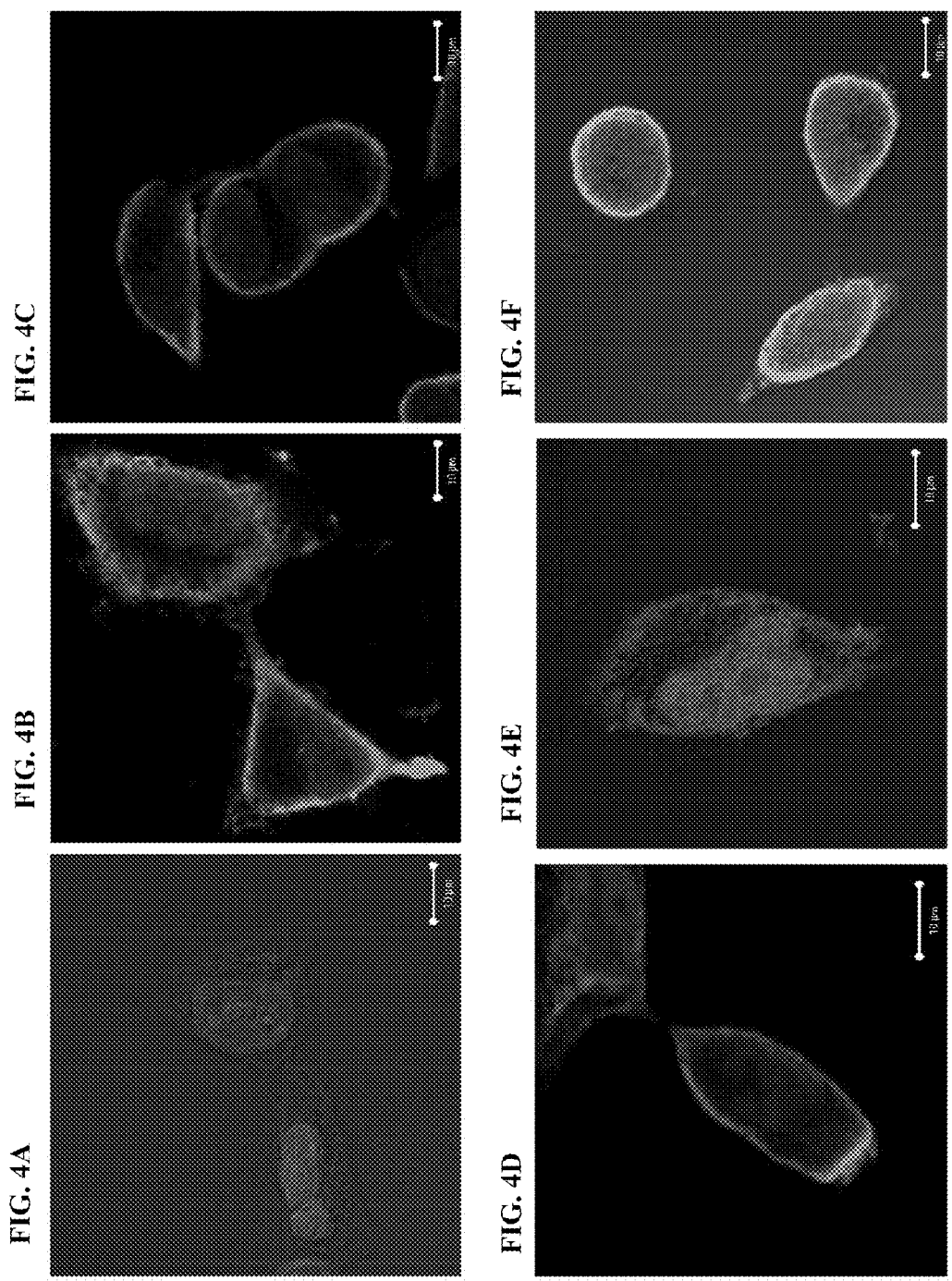

FIG. 7A FIG. 7B
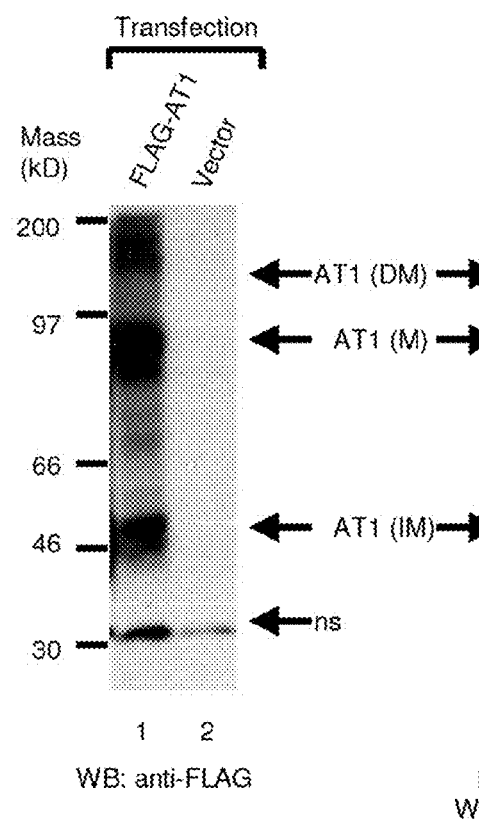
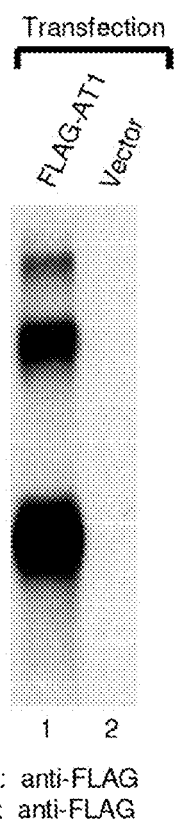
FIG. 7C
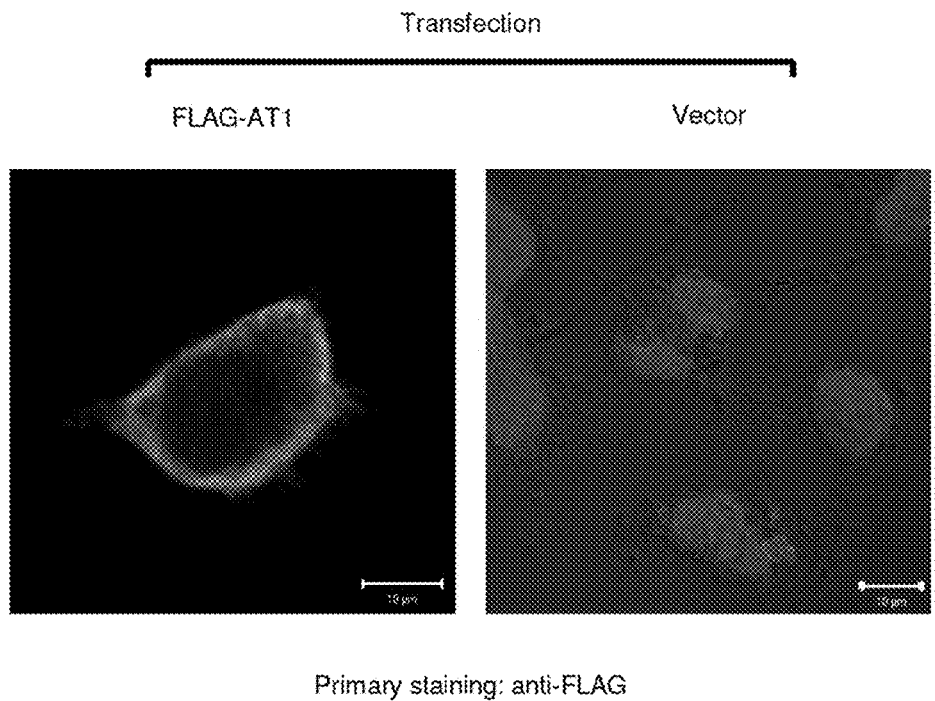

FIG. 9

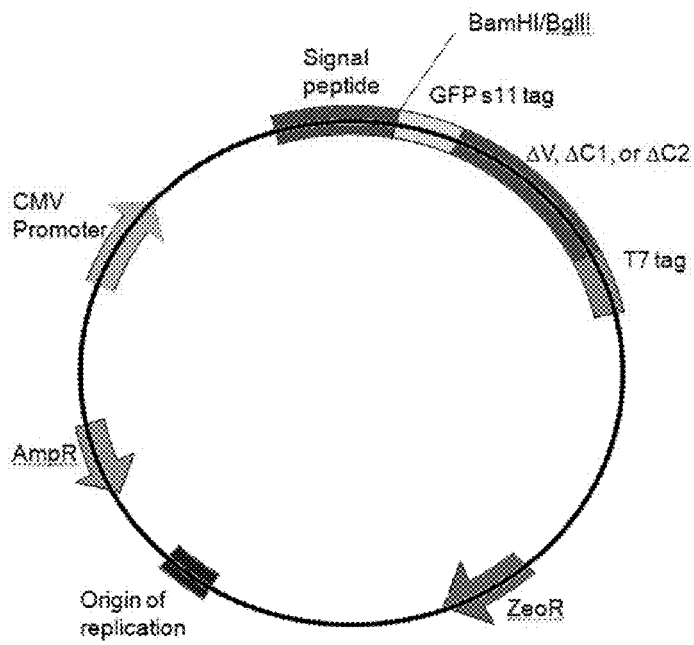

hRAGE Signal Peptide – directs mRNA to ER

GFP S11 tag – expresses strand 11 of green fluorescent protein

ΔV, ΔC1, or ΔC2 – Deletion mutants of hRAGE, lacking one of three domains

T7 ( gp10) tag – epitope recognized by antibodies

BamHI/BglI and XbaI Restriction Sites – nucleotide sequences that can be enzymatically cut and allow insertion

ZeocinR – confers resistance to Zeocin to plasmid

AmpicillinR – confers Ampicillin resistance to plasmid

Origin of replication – start site of DNA replication

CMV Promoter – allows plasmid expression in mammalian cells

SEQUENCE LISTING

```
<160> NUMBER OF SEQ ID NOS: 27

<210> SEQ ID NO 1
<211> LENGTH: 153
<212> TYPE: DNA
<213> ORGANISM: Artificial Sequence
<220> FEATURE:
<223> OTHER INFORMATION: Synthetic oligonucleotide

<400> SEQUENCE: 1
actagtatgg cagccggaac agcagttgga gcctgggtgc tggtcctcag tctgtggggg      60
gcagtagtag gtgctgaatt catggctagc atgactggtg gacagcaaat gggtactgga     120
tccggtacca agcttctcga gtctagaggg ccc                                  153

<210> SEQ ID NO 2
<211> LENGTH: 49
<212> TYPE: PRT
<213> ORGANISM: Artificial Sequence
<220> FEATURE:
<223> OTHER INFORMATION: Synthetic polypeptide

<400> SEQUENCE: 2

Met Ala Ala Gly Thr Ala Val Gly Ala Trp Val Leu Val Leu Ser Leu
1               5                   10                  15

Trp Gly Ala Val Val Gly Ala Glu Phe Met Ala Ser Met Thr Gly Gly
            20                  25                  30

Gln Gln Met Gly Thr Gly Ser Gly Thr Lys Leu Leu Glu Ser Arg Gly
        35                  40                  45

Pro

<210> SEQ ID NO 3
<211> LENGTH: 141
<212> TYPE: DNA
<213> ORGANISM: Artificial Sequence
<220> FEATURE:
<223> OTHER INFORMATION: Synthetic oligonucleotide

<400> SEQUENCE: 3
actagtatgg cagccggaac agcagttgga gcctgggtgc tggtcctcag tctgtggggg      60
gcagtagtag gtgctgaatt cgactacaaa gatgacgatg acaagggatc cggtaccaag     120
cttctcgagt ctagagggcc c                                               141

<210> SEQ ID NO 4
<211> LENGTH: 45
```

<212> TYPE: PRT
<213> ORGANISM: Artificial Sequence
<220> FEATURE:
<223> OTHER INFORMATION: Synthetic polypeptide

<400> SEQUENCE: 4

```
Met Ala Ala Gly Thr Ala Val Gly Ala Trp Val Leu Val Leu Ser Leu
1               5                   10                  15

Trp Gly Ala Val Val Gly Ala Glu Phe Asp Tyr Lys Asp Asp Asp Asp
            20                  25                  30

Lys Gly Ser Gly Thr Lys Leu Leu Glu Ser Arg Gly Pro
        35                  40                  45
```

<210> SEQ ID NO 5
<211> LENGTH: 1414
<212> TYPE: DNA
<213> ORGANISM: Homo sapiens
<220> FEATURE:
<221> NAME/KEY: CDS
<222> LOCATION: (25)..(1239)

<400> SEQUENCE: 5

```
gccaggaccc tggaaggaag cagg atg gca gcc gga aca gca gtt gga gcc        51
                          Met Ala Ala Gly Thr Ala Val Gly Ala
                          1               5 tgg gtg ctg gtc ctc agt ctg tgg ggg gca gta gta ggt gct caa aac       99
Trp Val Leu Val Leu Ser Leu Trp Gly Ala Val Val Gly Ala Gln Asn
10                  15                  20                  25 atc aca gcc cgg att ggc gag cca ctg gtg ctg aag tgt aag ggg gcc      147
Ile Thr Ala Arg Ile Gly Glu Pro Leu Val Leu Lys Cys Lys Gly Ala
                30                  35                  40 ccc aag aaa cca ccc cag cgg ctg gaa tgg aaa ctg aac aca ggc cgg      195
Pro Lys Lys Pro Pro Gln Arg Leu Glu Trp Lys Leu Asn Thr Gly Arg
            45                  50                  55 aca gaa gct tgg aag gtc ctg tct ccc cag gga gga ggc ccc tgg gac      243
Thr Glu Ala Trp Lys Val Leu Ser Pro Gln Gly Gly Gly Pro Trp Asp
        60                  65                  70 agt gtg gct cgt gtc ctt ccc aac ggc tcc ctc ttc ctt ccg gct gtc      291
Ser Val Ala Arg Val Leu Pro Asn Gly Ser Leu Phe Leu Pro Ala Val
    75                  80                  85 ggg atc cag gat gag ggg att ttc cgg tgc cag gca atg aac agg aat      339
Gly Ile Gln Asp Glu Gly Ile Phe Arg Cys Gln Ala Met Asn Arg Asn
90                  95                  100                 105 gga aag gag acc aag tcc aac tac cga gtc cgt gtc tac cag att cct      387
Gly Lys Glu Thr Lys Ser Asn Tyr Arg Val Arg Val Tyr Gln Ile Pro
                110                 115                 120 ggg aag cca gaa att gta gat tct gcc tct gaa ctc acg gct ggt gtt      435
Gly Lys Pro Glu Ile Val Asp Ser Ala Ser Glu Leu Thr Ala Gly Val
            125                 130                 135 ccc aat aag gtg ggg aca tgt gtg tca gag gga agc tac cct gca ggg      483
Pro Asn Lys Val Gly Thr Cys Val Ser Glu Gly Ser Tyr Pro Ala Gly
        140                 145                 150 act ctt agc tgg cac ttg gat ggg aag ccc ctg gtg cct aat gag aag      531
Thr Leu Ser Trp His Leu Asp Gly Lys Pro Leu Val Pro Asn Glu Lys
    155                 160                 165 gga gta tct gtg aag gaa cag acc agg aga cac cct gag aca ggg ctc      579
Gly Val Ser Val Lys Glu Gln Thr Arg Arg His Pro Glu Thr Gly Leu
170                 175                 180                 185 ttc aca ctg cag tcg gag cta atg gtg acc cca gcc cgg gga gga gat      627
Phe Thr Leu Gln Ser Glu Leu Met Val Thr Pro Ala Arg Gly Gly Asp
                190                 195                 200 ccc cgt ccc acc ttc tcc tgt agc ttc agc cca ggc ctt ccc cga cac      675
```

```
                                                                     -continued Pro Arg Pro Thr Phe Ser Cys Ser Phe Ser Pro Gly Leu Pro Arg His
                    205                 210                 215 cgg gcc ttg cgc aca gcc ccc atc cag ccc cgt gtc tgg gag cct gtg        723
Arg Ala Leu Arg Thr Ala Pro Ile Gln Pro Arg Val Trp Glu Pro Val
            220                 225                 230 cct ctg gag gag gtc caa ttg gtg gtg gag cca gaa ggt gga gca gta        771
Pro Leu Glu Glu Val Gln Leu Val Val Glu Pro Glu Gly Gly Ala Val
        235                 240                 245 gct cct ggt gga acc gta acc ctg acc tgt gaa gtc cct gcc cag ccc        819
Ala Pro Gly Gly Thr Val Thr Leu Thr Cys Glu Val Pro Ala Gln Pro
250                 255                 260                 265 tct cct caa atc cac tgg atg aag gat ggt gtg ccc ttg ccc ctt ccc        867
Ser Pro Gln Ile His Trp Met Lys Asp Gly Val Pro Leu Pro Leu Pro
                270                 275                 280 ccc agc cct gtg ctg atc ctc cct gag ata ggg cct cag gac cag gga        915
Pro Ser Pro Val Leu Ile Leu Pro Glu Ile Gly Pro Gln Asp Gln Gly
            285                 290                 295 acc tac agc tgt gtg gcc acc cat tcc agc cac ggg ccc cag gaa agc        963
Thr Tyr Ser Cys Val Ala Thr His Ser Ser His Gly Pro Gln Glu Ser
        300                 305                 310 cgt gct gtc agc atc agc atc atc gaa cca ggc gag gag ggg cca act       1011
Arg Ala Val Ser Ile Ser Ile Ile Glu Pro Gly Glu Glu Gly Pro Thr
    315                 320                 325 gca ggc tct gtg gga gga tca ggg ctg gga act cta gcc ctg gcc ctg       1059
Ala Gly Ser Val Gly Gly Ser Gly Leu Gly Thr Leu Ala Leu Ala Leu
330                 335                 340                 345 ggg atc ctg gga ggc ctg ggg aca gcc gcc ctg ctc att ggg gtc atc       1107
Gly Ile Leu Gly Gly Leu Gly Thr Ala Ala Leu Leu Ile Gly Val Ile
                350                 355                 360 ttg tgg caa agg cgg caa cgc cga gga gag gag agg aag gcc cca gaa       1155
Leu Trp Gln Arg Arg Gln Arg Arg Gly Glu Glu Arg Lys Ala Pro Glu
            365                 370                 375 aac cag gag gaa gag gag gag cgt gca gaa ctg aat cag tcg gag gaa       1203
Asn Gln Glu Glu Glu Glu Glu Arg Ala Glu Leu Asn Gln Ser Glu Glu
        380                 385                 390 cct gag gca ggc gag agt agt act gga ggg cct tga ggggcccaca            1249
Pro Glu Ala Gly Glu Ser Ser Thr Gly Gly Pro
    395                 400 gacagatccc atccatcagc tccctttttct ttttcccttg aactgttctg gcctcagacc    1309
aactctctcc tgtataatct ctctcctgta taaccccacc ttgccaagct ttcttctaca     1369
accagagccc cccacaatga tgattaaaca cctgacacat cttga                     1414

<210> SEQ ID NO 6
<211> LENGTH: 404
<212> TYPE: PRT
<213> ORGANISM: Homo sapiens

<400> SEQUENCE: 6

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80
```

```
Asn Gly Ser Leu Phe Leu Pro Ala Val Gly Ile Gln Asp Glu Gly Ile
                 85                  90                  95
Phe Arg Cys Gln Ala Met Asn Arg Asn Gly Lys Glu Thr Lys Ser Asn
            100                 105                 110
Tyr Arg Val Arg Val Tyr Gln Ile Pro Gly Lys Pro Glu Ile Val Asp
        115                 120                 125
Ser Ala Ser Glu Leu Thr Ala Gly Val Pro Asn Lys Val Gly Thr Cys
    130                 135                 140
Val Ser Glu Gly Ser Tyr Pro Ala Gly Thr Leu Ser Trp His Leu Asp
145                 150                 155                 160
Gly Lys Pro Leu Val Pro Asn Glu Lys Gly Val Ser Val Lys Glu Gln
                165                 170                 175
Thr Arg Arg His Pro Glu Thr Gly Leu Phe Thr Leu Gln Ser Glu Leu
            180                 185                 190
Met Val Thr Pro Ala Arg Gly Gly Asp Pro Arg Pro Thr Phe Ser Cys
        195                 200                 205
Ser Phe Ser Pro Gly Leu Pro Arg His Arg Ala Leu Arg Thr Ala Pro
    210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
        275                 280                 285
Pro Glu Ile Gly Pro Gln Asp Gln Gly Thr Tyr Ser Cys Val Ala Thr
    290                 295                 300
His Ser Ser His Gly Pro Gln Glu Ser Arg Ala Val Ser Ile Ser Ile
305                 310                 315                 320
Ile Glu Pro Gly Glu Glu Gly Pro Thr Ala Gly Ser Val Gly Gly Ser
                325                 330                 335
Gly Leu Gly Thr Leu Ala Leu Ala Leu Gly Ile Leu Gly Gly Leu Gly
            340                 345                 350
Thr Ala Ala Leu Leu Ile Gly Val Ile Leu Trp Gln Arg Arg Gln Arg
        355                 360                 365
Arg Gly Glu Glu Arg Lys Ala Pro Glu Asn Gln Glu Glu Glu Glu Glu
    370                 375                 380
Arg Ala Glu Leu Asn Gln Ser Glu Glu Pro Glu Ala Gly Glu Ser Ser
385                 390                 395                 400
Thr Gly Gly Pro

<210> SEQ ID NO 7
<211> LENGTH: 5667
<212> TYPE: DNA
<213> ORGANISM: Homo sapiens
<220> FEATURE:
<221> NAME/KEY: CDS
<222> LOCATION: (292)..(2811)

<400> SEQUENCE: 7
ctcttgctgt tctttagcc actggtctgc aggcgttttc ttcttctaac ttcctctcct    60
gtgacaaaag agataactat tagagaaaca aaagtccaga atgctaaggt tgccgctttc   120
acttcctctc acccttttagc ccagaactgc tttgaataca ccaattgctg tggggcggct   180
cgaggaagag aagacaccag tgcctcagaa actgctcggt cagacggtga tagcgagcca   240
```

-continued

```
cgcattcaca gggccactgc tgctcacaga agcagtgagg atgatgccag g atg atg      297
                                                         Met Met
                                                           1 tct gcc tcg cgc ctg gct ggg act ctg atc cca gcc atg gcc ttc ctc      345
Ser Ala Ser Arg Leu Ala Gly Thr Leu Ile Pro Ala Met Ala Phe Leu
        5              10              15 tcc tgc gtg aga cca gaa agc tgg gag ccc tgc gtg gag gtg gtt cct      393
Ser Cys Val Arg Pro Glu Ser Trp Glu Pro Cys Val Glu Val Val Pro
 20              25              30 aat att act tat caa tgc atg gag ctg aat ttc tac aaa atc ccc gac      441
Asn Ile Thr Tyr Gln Cys Met Glu Leu Asn Phe Tyr Lys Ile Pro Asp
 35              40              45              50 aac ctc ccc ttc tca acc aag aac ctg gac ctg agc ttt aat ccc ctg      489
Asn Leu Pro Phe Ser Thr Lys Asn Leu Asp Leu Ser Phe Asn Pro Leu
                 55              60              65 agg cat tta ggc agc tat agc ttc ttc agt ttc cca gaa ctg cag gtg      537
Arg His Leu Gly Ser Tyr Ser Phe Phe Ser Phe Pro Glu Leu Gln Val
         70              75              80 ctg gat tta tcc agg tgt gaa atc cag aca att gaa gat ggg gca tat      585
Leu Asp Leu Ser Arg Cys Glu Ile Gln Thr Ile Glu Asp Gly Ala Tyr
         85              90              95 cag agc cta agc cac ctc tct acc tta ata ttg aca gga aac ccc atc      633
Gln Ser Leu Ser His Leu Ser Thr Leu Ile Leu Thr Gly Asn Pro Ile
100             105             110 cag agt tta gcc ctg gga gcc ttt tct gga cta tca agt tta cag aag      681
Gln Ser Leu Ala Leu Gly Ala Phe Ser Gly Leu Ser Ser Leu Gln Lys
115             120             125             130 ctg gtg gct gtg gag aca aat cta gca tct cta gag aac ttc ccc att      729
Leu Val Ala Val Glu Thr Asn Leu Ala Ser Leu Glu Asn Phe Pro Ile
                135             140             145 gga cat ctc aaa act ttg aaa gaa ctt aat gtg gct cac aat ctt atc      777
Gly His Leu Lys Thr Leu Lys Glu Leu Asn Val Ala His Asn Leu Ile
        150             155             160 caa tct ttc aaa tta cct gag tat ttt tct aat ctg acc aat cta gag      825
Gln Ser Phe Lys Leu Pro Glu Tyr Phe Ser Asn Leu Thr Asn Leu Glu
        165             170             175 cac ttg gac ctt tcc agc aac aag att caa agt att tat tgc aca gac      873
His Leu Asp Leu Ser Ser Asn Lys Ile Gln Ser Ile Tyr Cys Thr Asp
        180             185             190 ttg cgg gtt cta cat caa atg ccc cta ctc aat ctc tct tta gac ctg      921
Leu Arg Val Leu His Gln Met Pro Leu Leu Asn Leu Ser Leu Asp Leu
195             200             205             210 tcc ctg aac cct atg aac ttt atc caa cca ggt gca ttt aaa gaa att      969
Ser Leu Asn Pro Met Asn Phe Ile Gln Pro Gly Ala Phe Lys Glu Ile
                215             220             225 agg ctt cat aag ctg act tta aga aat aat ttt gat agt tta aat gta      1017
Arg Leu His Lys Leu Thr Leu Arg Asn Asn Phe Asp Ser Leu Asn Val
        230             235             240 atg aaa act tgt att caa ggt ctg gct ggt tta gaa gtc cat cgt ttg      1065
Met Lys Thr Cys Ile Gln Gly Leu Ala Gly Leu Glu Val His Arg Leu
        245             250             255 gtt ctg gga gaa ttt aga aat gaa gga aac ttg gaa aag ttt gac aaa      1113
Val Leu Gly Glu Phe Arg Asn Glu Gly Asn Leu Glu Lys Phe Asp Lys
260             265             270 tct gct cta gag ggc ctg tgc aat ttg acc att gaa gaa ttc cga tta      1161
Ser Ala Leu Glu Gly Leu Cys Asn Leu Thr Ile Glu Glu Phe Arg Leu
275             280             285             290 gca tac tta gac tac tac ctc gat gat att att gac tta ttt aat tgt      1209
Ala Tyr Leu Asp Tyr Tyr Leu Asp Asp Ile Ile Asp Leu Phe Asn Cys
                295             300             305
```

```
ttg aca aat gtt tct tca ttt tcc ctg gtg agt gtg act att gaa agg      1257
Leu Thr Asn Val Ser Ser Phe Ser Leu Val Ser Val Thr Ile Glu Arg
        310                 315                 320 gta aaa gac ttt tct tat aat ttc gga tgg caa cat tta gaa tta gtt      1305
Val Lys Asp Phe Ser Tyr Asn Phe Gly Trp Gln His Leu Glu Leu Val
            325                 330                 335 aac tgt aaa ttt gga cag ttt ccc aca ttg aaa ctc aaa tct ctc aaa      1353
Asn Cys Lys Phe Gly Gln Phe Pro Thr Leu Lys Leu Lys Ser Leu Lys
340                 345                 350 agg ctt act ttc act tcc aac aaa ggt ggg aat gct ttt tca gaa gtt      1401
Arg Leu Thr Phe Thr Ser Asn Lys Gly Gly Asn Ala Phe Ser Glu Val
355                 360                 365                 370 gat cta cca agc ctt gag ttt cta gat ctc agt aga aat ggc ttg agt      1449
Asp Leu Pro Ser Leu Glu Phe Leu Asp Leu Ser Arg Asn Gly Leu Ser
                375                 380                 385 ttc aaa ggt tgc tgt tct caa agt gat ttt ggg aca acc agc cta aag      1497
Phe Lys Gly Cys Cys Ser Gln Ser Asp Phe Gly Thr Thr Ser Leu Lys
            390                 395                 400 tat tta gat ctg agc ttc aat ggt gtt att acc atg agt tca aac ttc      1545
Tyr Leu Asp Leu Ser Phe Asn Gly Val Ile Thr Met Ser Ser Asn Phe
        405                 410                 415 ttg ggc tta gaa caa cta gaa cat ctg gat ttc cag cat tcc aat ttg      1593
Leu Gly Leu Glu Gln Leu Glu His Leu Asp Phe Gln His Ser Asn Leu
    420                 425                 430 aaa caa atg agt gag ttt tca gta ttc cta tca ctc aga aac ctc att      1641
Lys Gln Met Ser Glu Phe Ser Val Phe Leu Ser Leu Arg Asn Leu Ile
435                 440                 445                 450 tac ctt gac att tct cat act cac acc aga gtt gct ttc aat ggc atc      1689
Tyr Leu Asp Ile Ser His Thr His Thr Arg Val Ala Phe Asn Gly Ile
                455                 460                 465 ttc aat ggc ttg tcc agt ctc gaa gtc ttg aaa atg gct ggc aat tct      1737
Phe Asn Gly Leu Ser Ser Leu Glu Val Leu Lys Met Ala Gly Asn Ser
            470                 475                 480 ttc cag gaa aac ttc ctt cca gat atc ttc aca gag ctg aga aac ttg      1785
Phe Gln Glu Asn Phe Leu Pro Asp Ile Phe Thr Glu Leu Arg Asn Leu
        485                 490                 495 acc ttc ctg gac ctc tct cag tgt caa ctg gag cag ttg tct cca aca      1833
Thr Phe Leu Asp Leu Ser Gln Cys Gln Leu Glu Gln Leu Ser Pro Thr
    500                 505                 510 gca ttt aac tca ctc tcc agt ctt cag gta cta aat atg agc cac aac      1881
Ala Phe Asn Ser Leu Ser Ser Leu Gln Val Leu Asn Met Ser His Asn
515                 520                 525                 530 aac ttc ttt tca ttg gat acg ttt cct tat aag tgt ctg aac tcc ctc      1929
Asn Phe Phe Ser Leu Asp Thr Phe Pro Tyr Lys Cys Leu Asn Ser Leu
                535                 540                 545 cag gtt ctt gat tac agt ctc aat cac ata atg act tcc aaa aaa cag      1977
Gln Val Leu Asp Tyr Ser Leu Asn His Ile Met Thr Ser Lys Lys Gln
            550                 555                 560 gaa cta cag cat ttt cca agt agt cta gct ttc tta aat ctt act cag      2025
Glu Leu Gln His Phe Pro Ser Ser Leu Ala Phe Leu Asn Leu Thr Gln
        565                 570                 575 aat gac ttt gct tgt act tgt gaa cac cag agt ttc ctg caa tgg atc      2073
Asn Asp Phe Ala Cys Thr Cys Glu His Gln Ser Phe Leu Gln Trp Ile
    580                 585                 590 aag gac cag agg cag ctc ttg gtg gaa gtt gaa cga atg gaa tgt gca      2121
Lys Asp Gln Arg Gln Leu Leu Val Glu Val Glu Arg Met Glu Cys Ala
595                 600                 605                 610 aca cct tca gat aag cag ggc atg cct gtg ctg agt ttg aat atc acc      2169
Thr Pro Ser Asp Lys Gln Gly Met Pro Val Leu Ser Leu Asn Ile Thr
                615                 620                 625
```

| | | | | | | | | | | | | | | | | |
|---|---|---|---|---|---|---|---|---|---|---|---|---|---|---|---|---|
| tgt | cag | atg | aat | aag | acc | atc | att | ggt | gtg | tcg | gtc | ctc | agt | gtg | ctt | 2217 |
| Cys | Gln | Met | Asn | Lys | Thr | Ile | Ile | Gly | Val | Ser | Val | Leu | Ser | Val | Leu | |
| | | | 630 | | | | 635 | | | | | 640 | | | | |
| gta | gta | tct | gtt | gta | gca | gtt | ctg | gtc | tat | aag | ttc | tat | ttt | cac | ctg | 2265 |
| Val | Val | Ser | Val | Val | Ala | Val | Leu | Val | Tyr | Lys | Phe | Tyr | Phe | His | Leu | |
| | | | | 645 | | | | | 650 | | | | | 655 | | |
| atg | ctt | ctt | gct | ggc | tgc | ata | aag | tat | ggt | aga | ggt | gaa | aac | atc | tat | 2313 |
| Met | Leu | Leu | Ala | Gly | Cys | Ile | Lys | Tyr | Gly | Arg | Gly | Glu | Asn | Ile | Tyr | |
| | 660 | | | | | 665 | | | | | 670 | | | | | |
| gat | gcc | ttt | gtt | atc | tac | tca | agc | cag | gat | gag | gac | tgg | gta | agg | aat | 2361 |
| Asp | Ala | Phe | Val | Ile | Tyr | Ser | Ser | Gln | Asp | Glu | Asp | Trp | Val | Arg | Asn | |
| 675 | | | | | 680 | | | | | 685 | | | | | 690 | |
| gag | cta | gta | aag | aat | tta | gaa | gaa | ggg | gtg | cct | cca | ttt | cag | ctc | tgc | 2409 |
| Glu | Leu | Val | Lys | Asn | Leu | Glu | Glu | Gly | Val | Pro | Pro | Phe | Gln | Leu | Cys | |
| | | | | 695 | | | | | 700 | | | | | 705 | | |
| ctt | cac | tac | aga | gac | ttt | att | ccc | ggt | gtg | gcc | att | gct | gcc | aac | atc | 2457 |
| Leu | His | Tyr | Arg | Asp | Phe | Ile | Pro | Gly | Val | Ala | Ile | Ala | Ala | Asn | Ile | |
| | | | 710 | | | | 715 | | | | | 720 | | | | |
| atc | cat | gaa | ggt | ttc | cat | aaa | agc | cga | aag | gtg | att | gtt | gtg | gtg | tcc | 2505 |
| Ile | His | Glu | Gly | Phe | His | Lys | Ser | Arg | Lys | Val | Ile | Val | Val | Val | Ser | |
| | | | | 725 | | | | | 730 | | | | | 735 | | |
| cag | cac | ttc | atc | cag | agc | cgc | tgg | tgt | atc | ttt | gaa | tat | gag | att | gct | 2553 |
| Gln | His | Phe | Ile | Gln | Ser | Arg | Trp | Cys | Ile | Phe | Glu | Tyr | Glu | Ile | Ala | |
| | 740 | | | | | 745 | | | | | 750 | | | | | |
| cag | acc | tgg | cag | ttt | ctg | agc | agt | cgt | gct | ggt | atc | atc | ttc | att | gtc | 2601 |
| Gln | Thr | Trp | Gln | Phe | Leu | Ser | Ser | Arg | Ala | Gly | Ile | Ile | Phe | Ile | Val | |
| 755 | | | | | 760 | | | | | 765 | | | | | 770 | |
| ctg | cag | aag | gtg | gag | aag | acc | ctg | ctc | agg | cag | cag | gtg | gag | ctg | tac | 2649 |
| Leu | Gln | Lys | Val | Glu | Lys | Thr | Leu | Leu | Arg | Gln | Gln | Val | Glu | Leu | Tyr | |
| | | | | 775 | | | | | 780 | | | | | 785 | | |
| cgc | ctt | ctc | agc | agg | aac | act | tac | ctg | gag | tgg | gag | gac | agt | gtc | ctg | 2697 |
| Arg | Leu | Leu | Ser | Arg | Asn | Thr | Tyr | Leu | Glu | Trp | Glu | Asp | Ser | Val | Leu | |
| | | | 790 | | | | 795 | | | | | 800 | | | | |
| ggg | cgg | cac | atc | ttc | tgg | aga | cga | ctc | aga | aaa | gcc | ctg | ctg | gat | ggt | 2745 |
| Gly | Arg | His | Ile | Phe | Trp | Arg | Arg | Leu | Arg | Lys | Ala | Leu | Leu | Asp | Gly | |
| | | 805 | | | | | 810 | | | | | 815 | | | | |
| aaa | tca | tgg | aat | cca | gaa | gga | aca | gtg | ggt | aca | gga | tgc | aat | tgg | cag | 2793 |
| Lys | Ser | Trp | Asn | Pro | Glu | Gly | Thr | Val | Gly | Thr | Gly | Cys | Asn | Trp | Gln | |
| | 820 | | | | | 825 | | | | | 830 | | | | | |
| gaa | gca | aca | tct | atc | tga | agaggaaaaa | | taaaaacctc | | ctgaggcatt | | | | | | 2841 |
| Glu | Ala | Thr | Ser | Ile | | | | | | | | | | | | |
| 835 | | | | | | | | | | | | | | | | | tcttgcccag ctgggtccaa cacttgttca gttaataagt attaaatgct gccacatgtc 2901 aggccttatg ctaagggtga gtaattccat ggtgcactag atatgcaggg ctgctaatct 2961 caaggagctt ccagtgcaga gggaataaat gctagactaa aatacagagt cttccaggtg 3021 ggcatttcaa ccaactcagt caaggaaccc atgacaaaga aagtcatttc aactcttacc 3081 tcatcaagtt gaataaagac agagaaaaca gaaagagaca ttgttctttt cctgagtctt 3141 ttgaatggaa attgtattat gttatagcca tcataaaacc attttggtag ttttgactga 3201 actgggtgtt cacttttttcc tttttgattg aatcaattt aaattctact tgatgactgc 3261 agtcgtcaag gggctcctga tgcaagatgc cccttccatt ttaagtctgt ctccttacag 3321 aggttaaagt ctagtggcta attcctaagg aaacctgatt aacacatgct cacaaccatc 3381 ctggtcattc tcgagcatgt tctattttt aactaatcac ccctgatata tttttatttt 3441 tatatatcca gttttcattt ttttacgtct tgcctataag ctaatatcat aaataaggtt 3501 gtttaagacg tgcttcaaat atccatatta accactattt ttcaaggaag tatggaaaag 3561

```
tacactctgt cactttgtca ctcgatgtca ttccaaagtt attgcctact aagtaatgac    3621
tgtcatgaaa gcagcattga ataaatttgt ttaaaggggg cactcttta aacgggaaga     3681 aaatttccgc ttcctggtct tatcatggac aatttgggct agaggcagga aggaagtggg    3741
atgacctcag gaggtcacct tttcttgatt ccagaaacat atgggctgat aaacccgggg    3801
tgacctcatg aaatgagttg cagcagaagt ttattttttt cagaacaagt gatgtttgat    3861
ggacctctga atctctttag ggagacacag atggctggga tccctcccct gtacccttct    3921
cactgccagg agaactacgt gtgaaggtat tcaaggcagg gagtatacat tgctgtttcc    3981
tgttgggcaa tgctccttga ccacattttg ggaagagtgg atgttatcat tgagaaaaca    4041
atgtgtctgg aattaatggg gttcttataa agaaggttcc cagaaaagaa tgttcatcca    4101
gcctcctcag aaacagaaca ttcaagaaaa ggacaatcag gatgtcatca gggaaatgaa    4161
aataaaaacc acaatgagat atcaccttat accaggtaga atggctacta taaaaaaatg    4221
aagtgtcatc aaggatatag agaaattgga acccttcttc actgctggag ggaatggaaa    4281
atggtgtagc cgttatgaaa aacagtacgg aggtttctca aaaattaaaa atagaactgc    4341
tatatgatcc agcaatctca cttctgtata tacccaaaa ataattgaaa tcagaatttc    4401
aagaaaatat ttacactccc atgttcattg tggcactctt cacaatcact gtttccaaag    4461
ttatggaaac aacccaaatt tccattgaaa aataaatgga caaagaaaat gtgcatatac    4521
gtacaatggg atattattca gcctaaaaaa agggggaatc ctgttattta tgacaacatg    4581
aataaacccg gaggccatta tgctatgtaa aatgagcaag taacagaaag acaaatactg    4641
cctgatttca tttatatgag gttctaaaat agtcaaactc atagaagcag agaatagaac    4701
agtggttcct agggaaaagg aggaagggag aaatgaggaa atagggagtt gtctaattgg    4761
tataaaatta tagtatgcaa gatgaattag ctctaaagat cagctgtata gcagagttcg    4821
tataatgaac aatactgtat tatgcactta acattttgtt aagagggtac ctctcatgtt    4881
aagtgttctt accatataca tatacacaag gaagcttttg gaggtgatgg atatatttat    4941
taccttgatt gtggtgatgg tttgacaggt atgtgactat gtctaaactc atcaaattgt    5001
atacattaaa tatatgcagt tttataatat caattatgtc tgaatgaagc tataaaaaag    5061
aaaagacaac aaaattcagt tgtcaaaact ggaaatatga ccacagtcag aagtgtttgt    5121
tactgagtgt ttcagagtgt gtttggtttg agcaggtcta gggtgattga acatccctgg    5181
gtgtgtttcc atgtctctcatg tactagtgaa agtagatgtg tgcatttgtg cacatatccc    5241
tatgtatccc tatcagggct gtgtgtattt gaaagtgtgt gtgtccgcat gatcatatct    5301
gtatagaaga gagtgtgatt atatttcttg aagaatacat ccatttgaaa tggatgtcta    5361
tggctgtttg agatgagttc tctactcttg tgcttgtaca gtagtctccc cttatcccctt    5421 atgcttggtg gatacgttct tagaccccaa gtggatctct gagaccgcag atggtaccaa    5481
acctcatata tgcaatattt tttcctatac ataaatacct aagataaagt tcatcttctg    5541
aattaggcac agtaagagat taacaataac taacaataaa attgaatagt tataataata    5601
tattgtaata aaagttatgt gaatgtgatc tctttctttc tctctctcaa aaaaaaaaa    5661 aaaaaa                                                                5667
```

<210> SEQ ID NO 8
<211> LENGTH: 839
<212> TYPE: PRT
<213> ORGANISM: Homo sapiens

<400> SEQUENCE: 8

```
Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
                35                  40                  45

Pro Asp Asn Leu Pro Phe Ser Thr Lys Asn Leu Asp Leu Ser Phe Asn
50                      55                  60

Pro Leu Arg His Leu Gly Ser Tyr Ser Phe Phe Ser Phe Pro Glu Leu
65                      70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
                100                 105                 110

Pro Ile Gln Ser Leu Ala Leu Gly Ala Phe Ser Gly Leu Ser Ser Leu
                115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
                180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
    210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
                260                 265                 270

Asp Lys Ser Ala Leu Glu Gly Leu Cys Asn Leu Thr Ile Glu Glu Phe
            275                 280                 285

Arg Leu Ala Tyr Leu Asp Tyr Tyr Leu Asp Asp Ile Ile Asp Leu Phe
    290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
                340                 345                 350

Leu Lys Arg Leu Thr Phe Thr Ser Asn Lys Gly Gly Asn Ala Phe Ser
            355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
```

```
                   420             425             430
Asn Leu Lys Gln Met Ser Glu Phe Ser Val Phe Leu Ser Leu Arg Asn
            435                 440                 445
Leu Ile Tyr Leu Asp Ile Ser His Thr His Thr Arg Val Ala Phe Asn
        450                 455                 460
Gly Ile Phe Asn Gly Leu Ser Ser Leu Glu Val Leu Lys Met Ala Gly
465                 470                 475                 480
Asn Ser Phe Gln Glu Asn Phe Leu Pro Asp Ile Phe Thr Glu Leu Arg
                485                 490                 495
Asn Leu Thr Phe Leu Asp Leu Ser Gln Cys Gln Leu Glu Gln Leu Ser
            500                 505                 510
Pro Thr Ala Phe Asn Ser Leu Ser Ser Leu Gln Val Leu Asn Met Ser
        515                 520                 525
His Asn Asn Phe Phe Ser Leu Asp Thr Phe Pro Tyr Lys Cys Leu Asn
    530                 535                 540
Ser Leu Gln Val Leu Asp Tyr Ser Leu Asn His Ile Met Thr Ser Lys
545                 550                 555                 560
Lys Gln Glu Leu Gln His Phe Pro Ser Ser Leu Ala Phe Leu Asn Leu
                565                 570                 575
Thr Gln Asn Asp Phe Ala Cys Thr Cys Glu His Gln Ser Phe Leu Gln
            580                 585                 590
Trp Ile Lys Asp Gln Arg Gln Leu Leu Val Glu Val Glu Arg Met Glu
        595                 600                 605
Cys Ala Thr Pro Ser Asp Lys Gln Gly Met Pro Val Leu Ser Leu Asn
610                 615                 620
Ile Thr Cys Gln Met Asn Lys Thr Ile Ile Gly Val Ser Val Leu Ser
625                 630                 635                 640
Val Leu Val Val Ser Val Val Ala Val Leu Val Tyr Lys Phe Tyr Phe
                645                 650                 655
His Leu Met Leu Leu Ala Gly Cys Ile Lys Tyr Gly Arg Gly Glu Asn
            660                 665                 670
Ile Tyr Asp Ala Phe Val Ile Tyr Ser Ser Gln Asp Glu Asp Trp Val
        675                 680                 685
Arg Asn Glu Leu Val Lys Asn Leu Glu Glu Gly Val Pro Pro Phe Gln
690                 695                 700
Leu Cys Leu His Tyr Arg Asp Phe Ile Pro Gly Val Ala Ile Ala Ala
705                 710                 715                 720
Asn Ile Ile His Glu Gly Phe His Lys Ser Arg Lys Val Ile Val Val
                725                 730                 735
Val Ser Gln His Phe Ile Gln Ser Arg Trp Cys Ile Phe Glu Tyr Glu
            740                 745                 750
Ile Ala Gln Thr Trp Gln Phe Leu Ser Ser Arg Ala Gly Ile Ile Phe
        755                 760                 765
Ile Val Leu Gln Lys Val Glu Lys Thr Leu Leu Arg Gln Gln Val Glu
770                 775                 780
Leu Tyr Arg Leu Leu Ser Arg Asn Thr Tyr Leu Glu Trp Glu Asp Ser
785                 790                 795                 800
Val Leu Gly Arg His Ile Phe Trp Arg Arg Leu Arg Lys Ala Leu Leu
                805                 810                 815
Asp Gly Lys Ser Trp Asn Pro Glu Gly Thr Val Gly Thr Gly Cys Asn
            820                 825                 830
Trp Gln Glu Ala Thr Ser Ile
        835
```

-continued

```
<210> SEQ ID NO 9
<211> LENGTH: 2420
<212> TYPE: DNA
<213> ORGANISM: Homo sapiens
<220> FEATURE:
<221> NAME/KEY: CDS
<222> LOCATION: (447)..(1526)

<400> SEQUENCE: 9
actataaatt cggagctgcc tcctcgccaa tgattccagc gcctgacagc caggacccca      60
ggcagcagcg agtgacagga cgtctggacc ggcgcgccgc tagcagctct gccgggccgc     120
ggcggtgatc gatggggagc ggctggagcg gacccagcga gtgagggcgc acagccggga     180
cgccgaggcg gcgggcggga gacccgcacc agcgcagccg gccctcggcg ggacgtgacg     240
cagcgcccgg ggcgcgggtt tgatatttga caaattgatc taaaatggct gggttttttat    300 ctgaataact cactgatgcc atcccagaaa gtcggcacca gatgaagaaa atgaatcaca     360
agtcaactga cagtccaaag gctccacagc tcagaggagg tgtatttgat atagtgtttg     420
caacaaattc gacccaggtg atcaaa atg att ctc aac tct tct act gaa gat      473
                              Met Ile Leu Asn Ser Ser Thr Glu Asp
                                1               5 ggt att aaa aga atc caa gat gat tgt ccc aaa gct gga agg cat aat       521
Gly Ile Lys Arg Ile Gln Asp Asp Cys Pro Lys Ala Gly Arg His Asn
 10              15                  20                  25 tac ata ttt gtc atg att cct act tta tac agt atc atc ttt gtg gtg       569
Tyr Ile Phe Val Met Ile Pro Thr Leu Tyr Ser Ile Ile Phe Val Val
             30                  35                  40 gga ata ttt gga aac agc ttg gtg gtg ata gtc att tac ttt tat atg       617
Gly Ile Phe Gly Asn Ser Leu Val Val Ile Val Ile Tyr Phe Tyr Met
         45                  50                  55 aag ctg aag act gtg gcc agt gtt ttt ctt ttg aat tta gca ctg gct       665
Lys Leu Lys Thr Val Ala Ser Val Phe Leu Leu Asn Leu Ala Leu Ala
     60                  65                  70 gac tta tgc ttt tta ctg act ttg cca cta tgg gct gtc tac aca gct       713
Asp Leu Cys Phe Leu Leu Thr Leu Pro Leu Trp Ala Val Tyr Thr Ala
 75                  80                  85 atg gaa tac cgc tgg ccc ttt ggc aat tac cta tgt aag att gct tca       761
Met Glu Tyr Arg Trp Pro Phe Gly Asn Tyr Leu Cys Lys Ile Ala Ser
 90                  95                 100                 105 gcc agc gtc agt ttc aac ctg tac gct agt gtg ttt cta ctc acg tgt       809
Ala Ser Val Ser Phe Asn Leu Tyr Ala Ser Val Phe Leu Leu Thr Cys
             110                 115                 120 ctc agc att gat cga tac ctg gct att gtt cac cca atg aag tcc cgc       857
Leu Ser Ile Asp Arg Tyr Leu Ala Ile Val His Pro Met Lys Ser Arg
         125                 130                 135 ctt cga cgc aca atg ctt gta gcc aaa gtc acc tgc atc atc att tgg       905
Leu Arg Arg Thr Met Leu Val Ala Lys Val Thr Cys Ile Ile Ile Trp
     140                 145                 150 ctg ctg gca ggc ttg gcc agt ttg cca gct ata atc cat cga aat gta       953
Leu Leu Ala Gly Leu Ala Ser Leu Pro Ala Ile Ile His Arg Asn Val
 155                 160                 165 ttt ttc att gag aac acc aat att aca gtt tgt gct ttc cat tat gag      1001
Phe Phe Ile Glu Asn Thr Asn Ile Thr Val Cys Ala Phe His Tyr Glu
 170                 175                 180                 185 tcc caa aat tca acc ctc ccg ata ggg ctg ggc ctg acc aaa aat ata      1049
Ser Gln Asn Ser Thr Leu Pro Ile Gly Leu Gly Leu Thr Lys Asn Ile
             190                 195                 200 ctg ggt ttc ctg ttt cct ttc ctg atc att ctt aca agt tat act ctt      1097
Leu Gly Phe Leu Phe Pro Phe Leu Ile Ile Leu Thr Ser Tyr Thr Leu
         205                 210                 215
```

| | | | | | | | | | | | | | | | |
|---|---|---|---|---|---|---|---|---|---|---|---|---|---|---|---|
| att | tgg | aag | gcc | cta | aag | aag | gct | tat | gaa | att | cag | aag | aac | aaa | cca | 1145
| Ile | Trp | Lys | Ala | Leu | Lys | Lys | Ala | Tyr | Glu | Ile | Gln | Lys | Asn | Lys | Pro |
| | 220 | | | | 225 | | | | | 230 | | | | | |

| aga | aat | gat | gat | att | ttt | aag | ata | att | atg | gca | att | gtg | ctt | ttc | ttt | 1193 |
| Arg | Asn | Asp | Asp | Ile | Phe | Lys | Ile | Ile | Met | Ala | Ile | Val | Leu | Phe | Phe |
| 235 | | | | | 240 | | | | | 245 | | | | | |

| ttc | ttt | tcc | tgg | att | ccc | cac | caa | ata | ttc | act | ttt | ctg | gat | gta | ttg | 1241 |
| Phe | Phe | Ser | Trp | Ile | Pro | His | Gln | Ile | Phe | Thr | Phe | Leu | Asp | Val | Leu |
| 250 | | | | 255 | | | | | 260 | | | | | | 265 |

| att | caa | cta | ggc | atc | ata | cgt | gac | tgt | aga | att | gca | gat | att | gtg | gac | 1289 |
| Ile | Gln | Leu | Gly | Ile | Ile | Arg | Asp | Cys | Arg | Ile | Ala | Asp | Ile | Val | Asp |
| | | | 270 | | | | 275 | | | | | 280 | | | |

| acg | gcc | atg | cct | atc | acc | att | tgt | ata | gct | tat | ttt | aac | aat | tgc | ctg | 1337 |
| Thr | Ala | Met | Pro | Ile | Thr | Ile | Cys | Ile | Ala | Tyr | Phe | Asn | Asn | Cys | Leu |
| | | | 285 | | | | 290 | | | | | 295 | | | |

| aat | cct | ctt | ttt | tat | ggc | ttt | ctg | ggg | aaa | aaa | ttt | aaa | aga | tat | ttt | 1385 |
| Asn | Pro | Leu | Phe | Tyr | Gly | Phe | Leu | Gly | Lys | Lys | Phe | Lys | Arg | Tyr | Phe |
| | | 300 | | | | | 305 | | | | | 310 | | | |

| ctc | cag | ctt | cta | aaa | tat | att | ccc | cca | aaa | gcc | aaa | tcc | cac | tca | aac | 1433 |
| Leu | Gln | Leu | Leu | Lys | Tyr | Ile | Pro | Pro | Lys | Ala | Lys | Ser | His | Ser | Asn |
| | 315 | | | | | 320 | | | | | 325 | | | | |

| ctt | tca | aca | aaa | atg | agc | acg | ctt | tcc | tac | cgc | ccc | tca | gat | aat | gta | 1481 |
| Leu | Ser | Thr | Lys | Met | Ser | Thr | Leu | Ser | Tyr | Arg | Pro | Ser | Asp | Asn | Val |
| 330 | | | | | 335 | | | | | 340 | | | | | 345 |

| agc | tca | tcc | acc | aag | aag | cct | gca | cca | tgt | ttt | gag | gtt | gag | tga | | 1526 |
| Ser | Ser | Ser | Thr | Lys | Lys | Pro | Ala | Pro | Cys | Phe | Glu | Val | Glu | | |
| | | | 350 | | | | | 355 | | | | | | | | catgttcgaa acctgtccat aaagtaattt tgtgaaagaa ggagcaagag aacattcctc 1586 tgcagcactt cactaccaaa tgagcattag ctacttttca gaattgaagg agaaaatgca 1646 ttatgtggac tgaaccgact tttctaaagc tctgaacaaa agcttttctt tccttttgca 1706 acaagacaaa gcaaagccac attttgcatt agacagatga cggctgctcg aagaacaatg 1766 tcagaaactc gatgaatgtg ttgatttgag aaattttact gacagaaatg caatctccct 1826 agcctgcttt tgtcctgtta ttttttattt ccacataaag gtatttagaa tatattaaat 1886 cgttagagga gcaacaggag atgagagttc cagattgttc tgtccagttt ccaagggca 1946 gtaaagtttt cgtgccggtt ttcagctatt agcaactgtg ctacacttgc acctggtact 2006 gcacattttg tacaaagata tgctaagcag tagtcgtcaa gttgcagatc tttttgtgaa 2066 attcaacctg tgtcttatag gtttacactg ccaaaacaat gcccgtaaga tggcttattt 2126 gtataatggt gttactaaag tcacatataa aagttaaact acttgtaaag gtgctgcact 2186 ggtcccaagt agtagtgtct tcctagtata ttagtttgat ttaatatctg agaagtgtat 2246 atagtttgtg gtaaaaagat tatatatcat aaagtatgcc ttcctgttta aaaaagtat 2306 atattctaca catatatgta tatgtatatc tatatctcta aactgctgtt aattgattaa 2366 aatctggcaa agttatattt actttaaaat aaaataattt tattgcaaaa aaaa 2420

<210> SEQ ID NO 10
<211> LENGTH: 359
<212> TYPE: PRT
<213> ORGANISM: Homo sapiens

<400> SEQUENCE: 10

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

```
Thr Leu Tyr Ser Ile Ile Phe Val Val Gly Ile Phe Gly Asn Ser Leu
            35                  40                  45

Val Val Ile Val Ile Tyr Phe Tyr Met Lys Leu Lys Thr Val Ala Ser
 50                  55                  60

Val Phe Leu Leu Asn Leu Ala Leu Ala Asp Leu Cys Phe Leu Leu Thr
 65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
            115                 120                 125

Ala Ile Val His Pro Met Lys Ser Arg Leu Arg Arg Thr Met Leu Val
        130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
            195                 200                 205

Leu Ile Ile Leu Thr Ser Tyr Thr Leu Ile Trp Lys Ala Leu Lys Lys
        210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
        290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
            325                 330                 335

Leu Ser Tyr Arg Pro Ser Asp Asn Val Ser Ser Ser Thr Lys Lys Pro
            340                 345                 350

Ala Pro Cys Phe Glu Val Glu
            355

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Met Ala Ser Met Thr Gly Gly Gln Gln Met Gly Thr
1               5                   10

<210> SEQ ID NO 12
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 12

Asp Tyr Lys Asp Asp Asp Asp Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Tyr Pro Tyr Asp Val Pro Asp Tyr Ala
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Tyr Thr Asp Ile Glu Met Asn Arg Leu Gly Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic peptide

<400> SEQUENCE: 15

Gly Lys Pro Ile Pro Asn Pro Leu Leu Gly Leu Asp Ser Thr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Glu Gln Lys Leu Ile Ser Glu Glu Asp Leu
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

His His His His His His
1               5

<210> SEQ ID NO 18
<211> LENGTH: 4
<212> TYPE: PRT
<213> ORGANISM: Homo sapiens
```

<400> SEQUENCE: 18

Gln Asn Ile Thr
1

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Asp Asp Asp Asp Lys
1               5

<210> SEQ ID NO 20
<211> LENGTH: 78
<212> TYPE: DNA
<213> ORGANISM: Artificial Sequence
<220> FEATURE:
<223> OTHER INFORMATION: Synthetic nucleic acid

<400> SEQUENCE: 20
cgggaccaca tggtgctgca cgagtacgtg aacgccgccg gcatcacagg cgacggcggc    60
agcggcggcg gcggcgac                                                  78

<210> SEQ ID NO 21
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (17)..(26)
<223> OTHER INFORMATION: poly G linker

<400> SEQUENCE: 21

Arg Asp His Met Val Leu His Glu Tyr Val Asn Ala Ala Gly Ile Thr
1               5                   10                  15

Gly Asp Gly Gly Ser Gly Gly Gly Gly Asp
            20                  25

<210> SEQ ID NO 22
<211> LENGTH: 651
<212> TYPE: DNA
<213> ORGANISM: Artificial Sequence
<220> FEATURE:
<223> OTHER INFORMATION: Synthetic nucleic acid

<400> SEQUENCE: 22
atgagcaaag gagaagaact tttcactgga gttgtcccaa ttcttgttga attagatggt    60
gatgttaatg ggcacaaatt ttctgtcaga ggagagggtg aaggtgatgc tacaatcgga   120
aaactcaccc ttaaatttat ttgcactact ggaaaactac ctgttccatg gccaacactt   180
gtcactactc tgacctatgg tgttcaatgc ttttcccgtt atccggatca catgaaaagg   240
catgactttt tcaagagtgc catgcccgaa ggttatgtac aggaacgcac tatatctttc   300
aaagatgacg ggaaatacaa gacgcgtgct gtagtcaagt tgaaggtga tacccttgtt    360 aatcgtatcg agttaaaggg tactgatttt aaagaagatg gaaacattct cggacacaaa   420
ctcgagtaca actttaactc acacaatgta tacatcacgg cagacaaaca aaagaatgga   480
atcaaagcta acttcacagt tcgccacaac gttgaagatg gttccgttca actagcagac   540
cattatcaac aaaatactcc aattggcgat ggccctgtcc ttttaccaga caaccattac 600
ctgtcgacac aaactgtcct ttcgaaagat cccaacgaaa agggtaccta a 651

<210> SEQ ID NO 23
<211> LENGTH: 214
<212> TYPE: PRT
<213> ORGANISM: Artificial Sequence
<220> FEATURE:
<223> OTHER INFORMATION: Synthetic peptide

<400> SEQUENCE: 23

Met Ser Lys Gly Glu Glu Leu Phe Thr Gly Trp Pro Ile Leu Val Glu
1               5                   10                  15

Leu Asp Gly Asp Val Asn Gly His Lys Phe Ser Val Arg Gly Glu Gly
            20                  25                  30

Glu Gly Asp Ala Thr Ile Gly Lys Leu Thr Leu Lys Phe Ile Cys Thr
        35                  40                  45

Thr Gly Lys Leu Pro Val Pro Trp Pro Thr Leu Val Thr Thr Leu Thr
    50                  55                  60

Tyr Gly Val Gln Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Lys Tyr Lys Thr Arg Ala Trp Lys Phe
            100                 105                 110

Glu Gly Asp Thr Leu Val Asn Arg Ile Glu Leu Lys Gly Thr Asp Phe
        115                 120                 125

Lys Glu Asp Gly Asn Ile Leu Gly His Lys Leu Glu Tyr Asn Phe Asn
    130                 135                 140

Ser His Asn Val Tyr Ile Thr Ala Asp Lys Gln Lys Asn Gly Ile Lys
145                 150                 155                 160

Ala Asn Phe Thr Val Arg His Asn Val Glu Asp Gly Ser Val Gln Leu
                165                 170                 175

Ala Asp His Tyr Gln Gln Asn Thr Pro Ile Gly Asp Gly Pro Val Leu
            180                 185                 190

Leu Pro Asp Asn His Tyr Leu Ser Thr Gln Thr Val Leu Ser Lys Asp
        195                 200                 205

Pro Asn Glu Lys Gly Thr
    210

<210> SEQ ID NO 24
<211> LENGTH: 84
<212> TYPE: DNA
<213> ORGANISM: Artificial Sequence
<220> FEATURE:
<223> OTHER INFORMATION: Synthetic nucleic acid

<400> SEQUENCE: 24
gagaagcggg accacatggt gctgctggag tacgtgaccg ccgccggcat cacaggcgac    60
ggcggcagcg gcggcggcgg cgac    84

<210> SEQ ID NO 25
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<222> LOCATION: (19)..(28)
<223> OTHER INFORMATION: poly G linker

<400> SEQUENCE: 25

Glu Lys Arg Asp His Met Val Leu Leu Glu Tyr Val Thr Ala Ala Gly
1               5                   10                  15

Ile Thr Gly Asp Gly Gly Ser Gly Gly Gly Asp
            20                  25

<210> SEQ ID NO 26
<211> LENGTH: 84
<212> TYPE: DNA
<213> ORGANISM: Artificial Sequence
<220> FEATURE:
<223> OTHER INFORMATION: Synthetic nucleic acid

<400> SEQUENCE: 26
ctgcctgacg accactacct gtctacccag accatcctgt ctaaggacct gaacggcgac      60
ggcggcagcg gcggcggcgg cgac                                            84

<210> SEQ ID NO 27
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (19)..(28)
<223> OTHER INFORMATION: poly G linker

<400> SEQUENCE: 27

Leu Pro Asp Asp His Tyr Leu Ser Thr Gln Thr Ile Leu Ser Lys Asp
1               5                   10                  15

Leu Asn Gly Asp Gly Gly Ser Gly Gly Gly Asp
            20                  25
```

NUCLEIC ACID MODULES FOR EXPRESSION AND TAGGING OF MEMBRANE PROTEINS AND METHODS OF USE

CROSS REFERENCE TO RELATED APPLICATIONS

This application claims the benefit of U.S. Provisional Application No. 61/142,531, filed on Jan. 5, 2009, which is herein incorporated by reference in its entirety.

FIELD

This disclosure concerns expression and tagging of membrane proteins. In particular, this disclosure relates to nucleic acid modules for subcloning, tagging and expressing mammalian membrane proteins in cells.

BACKGROUND

Expression of a mammalian protein in laboratory cell lines is the most common approach used to study its biological functions, including localization, trafficking, translocation and interaction with other cellular factors (Chen et al., *Proc Natl Acad Sci USA* 90:6508-6512, 1993; Lemas et al., *J Biol Chem* 269:18651-18655, 1994; Molloy et al., *EMBO J* 13:18-33, 1994; Quon et al., *Proc Natl Acad Sci USA* 91:5587-5591, 1994). This approach can also serve to produce laboratory or industrial scale quantities of recombinant proteins, for instance for structural studies or therapeutic purposes (Grisshanuner and Tate, *Q Rev Biophys* 28:315-422, 1995; Mather et al., *Methods Mol Biol* 62:369-382, 1997; Freimuth, *Genet Eng* 28:95-104, 2007). Although overexpression in bacterial cells is often used to produce proteins on a large scale, in many cases the expressed mammalian proteins, especially membrane proteins, either mis-fold or do not retain proper function due to the lack of necessary posttranslational modifications. Mammalian proteins can be sub-cloned into a mammalian promoter-driven expression vector and expressed in a commonly used laboratory cell line, such as Chinese hamster ovary (CHO) cells, human embryonic kidney 293 (HEK 293) cells, HeLa (cervical cancer) cells, or NIH 3T3 (mouse embryonic fibroblast) cells, for the aforementioned purposes.

Oftentimes, this strategy relies on the availability of antibodies to the target protein for detection and confirmation that it is being expressed. Thus, the intended studies are problematic for newly discovered proteins against which no antibodies have been generated, or when the effectiveness or the specificity of the antibody is in question. These difficulties are circumvented if the target protein is tagged with a short epitope tag to which an effective antibody is available. Epitope-tagging a protein also facilitates the purification of the target protein, as antibodies to the epitope tag can be immobilized to matrixes for affinity chromatography (Jarvik and Telmer, *Annu Rev Genet* 32:601-618, 1998; Fritze and Anderson, *Methods Enzymol* 327:3-16, 2000).

Expressing and tagging soluble mammalian proteins is relatively simple, as expression vectors with various epitope tags and multicloning sites are widely available, and the subcloning process is straightforward. In contrast, expressing and studying membrane proteins in laboratory cell lines is more technically challenging. First, effective antibodies specific for membrane proteins are often difficult to generate. Second, because the majority of membrane proteins possess a signal peptide at their N-terminus that directs co-translational translocation of membrane proteins into the endoplasmic reticulum (ER) for cell surface expression, and this short peptide is proteolytically cleaved within the ER, tagging at the N-terminus of a membrane protein involves insertion of the epitope tag between the signal peptide and the mature membrane protein. Tagging at the N-terminus is often preferred, especially for Type Ia membrane proteins, the class to which most eukaryotic membrane proteins with single membrane-spanning regions belong. Since this group of membrane proteins exposes their N-terminus on the exterior side of the plasma membrane, tagging at the N-terminus may avoid possible functional interferences of their C-terminal, cytosolic portion, which often serves as the signal domain. In addition, the exterior portion of membrane proteins is often glycosylated, which is required for full biological function. Therefore, N-terminal tagging can interfere with the post-translational modification of membrane proteins.

Vectors with signal peptides and epitope tags have been previously constructed and used in various studies (Guan et al., *J Biol Chem* 267:21995-21998, 1992; Kobilka, *Anal Biochem* 231:269-271, 1995; den Hertog and Hunter, *EMBO J* 15:3016-3027, 1996; Zhou et al., *Mol Immunol* 33:1127-1134, 1996). However, these vectors were tailored for the expression of individual membrane proteins. They therefore have limited cloning sites available for the adaptation of either different epitope tags, or a variety of membrane proteins. Some signal peptides also result in cytotoxicity that leads to either mutations or lower expression level of the membrane protein when it is expressed heterologously. Thus, a need exists to develop mammalian expression modules that can be adapted to subclone, tag, and express a variety of mammalian membrane proteins in common laboratory cell lines.

SUMMARY

Disclosed herein are nucleic acid modules for expression and tagging of membrane proteins. The disclosed modules can be used universally with any type of membrane protein and any type of protein tag for the expression, detection and/or isolation of the membrane protein. The modules comprise, in the 5' to 3' direction, (i) a nucleic acid sequence encoding the signal peptide of Receptor for Advanced Glycation End products (RAGE); (ii) a nucleic acid sequence encoding a tag; and (iii) a multiple cloning site (MCS). The tag can be any protein tag suitable to allow for expression and translocation of a membrane protein, such as an immunogenic epitope tag, affinity tag or fluorescent protein, or fragment of a fluorescent protein. The MCS can contain any number of unique restriction enzyme recognition sequences, such as at least two, at least three, at least four, at least five, or at least six or more different restriction enzyme recognition sequences. In some embodiments, the nucleic acid module further includes the coding sequence of a membrane protein inserted into the MCS. In particular examples, the membrane protein is a Type I membrane protein or a Type III membrane protein. In some embodiments, the nucleic acid module further includes a protease cleavage sequence 3' of the epitope tag. In some embodiments, the nucleic acid module further includes a second tag at the 3' end of the module.

Also provided are vectors comprising the disclosed nucleic acid modules, and isolated cells comprising the vectors.

Further provided is a method of expressing and tagging a membrane protein. The method includes cloning the coding sequence of the membrane protein into the MCS of a vector comprising a nucleic acid module disclosed herein. In some embodiments, the method further comprises transfecting a cell with the vector under conditions sufficient to allow for expression of the membrane protein.

The foregoing and other objects, features, and advantages of the invention will become more apparent from the following detailed description, which proceeds with reference to the accompanying figures.

BRIEF DESCRIPTION OF THE FIGURES

FIGS. 1A-1D show the nucleotide and amino acid sequences of representative designed modules. (A) Nucleotide sequence of a T7 epitope tag module (SEQ ID NO: 1). Hexamer sequences that are recognized by restriction enzymes are marked at the top of the first base and labeled beneath with name of the enzyme. The ApaI (GGGCCC) site is acquired after ligation with pCDNA3.1 vector as an additional in-frame cloning site. (B) Peptide sequence of the same T7 epitope tag module (SEQ ID NO: 2). Amino acid residues corresponding to the human RAGE signal peptide, T7 tag, and MCS sequences are indicated. (C) Nucleotide sequence of a FLAG epitope tag module (SEQ ID NO: 3). Hexamer sequences that are recognized by restriction enzymes are marked at the top of the first base and labeled beneath with name of the enzyme. (D) Peptide sequence of the same FLAG epitope tag module (SEQ ID NO: 4). Amino acid residues corresponding to the human RAGE signal peptide, FLAG tag, and MCS sequences are indicated.

FIGS. 4A-4F are confocal microscopy images showing epitope-tagged RAGE and TLR4 are expressed at the cell surface. Both tagged RAGE and TLR4 were transfected into HEK 293 cells and immunohistochemistry was performed. (A) Vector-transfected HEK 293 cells stained with anti-T7 and anti-FLAG antibodies (negative control). (B) T7-RAGE transfected HEK 293 stained with anti-T7 antibodies. (C) FLAG-RAGE transfected HEK 293 stained with anti-FLAG antibodies. (D) FLAG-TLR4 transfected HEK 293 cells stained with anti-TLR4 antibodies. (E) T7-TLR4 transfected HEK 293 cells stained with anti-T7 antibodies. (F) FLAG-TLR4 transfected cells stained with anti-FLAG antibodies. Each representative image was selected from at least three independent staining experiments.

FIGS. 7A-7C show expression of FLAG-tagged AT1 in HEK293 cells. (A) WB of FLAG-AT1. Glycosylated and unglycosylated forms are indicated (M=mature AT1; IM=immature AT1; DM=dimerized AT1; ns=non-specific). (B) IP of FLAG-AT1. IP was performed using mouse anti-FLAG antibodies (M2) and WB was performed using mouse anti-FLAG antibodies (M2, peroxidase conjugate). (C) FLAG-tagged AT1 is expressed at the cell surface. FLAG-AT1 was transfected into HEK 293 cells and stained with anti-FLAG antibody. Shown are a FLAG-AT1 transfected cell (left panel) and vector-transfected cells (right panel). Each representative image was selected from at least three independent staining experiments.

FIG. 9 is a schematic showing the plasmid map for hRAGE ΔV, ΔC1, and ΔC2 deletion mutants tagged with spGFP S11.

SEQUENCE LISTING

Figure 2A:
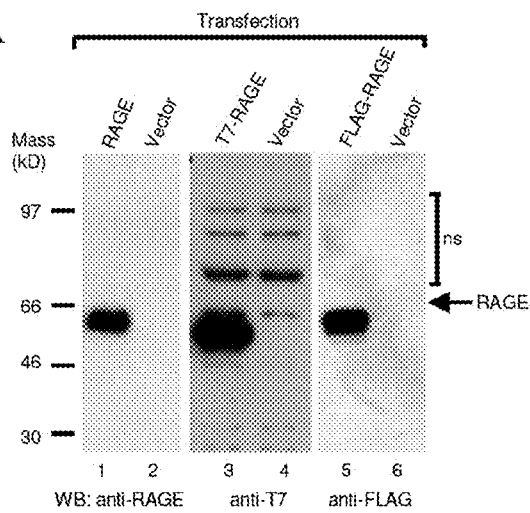
FIGS. 2A-2C show detection of epitope-tagged human RAGE by Western blot (WB) and immunoprecipitation (IP). (A) The expressed epitope-tagged RAGE proteins are recognized by antibodies to the tags. Untagged and tagged RAGE constructs were transfected into CHO-CD14 cells, and cell lysates were resolved with SDS-PAGE in 4-12% pre-cast Bis-Tris gel (Invitrogen). The transferred membranes were blotted with antibodies to RAGE (lanes 1 and 2), and either anti-T7 antibodies (lanes 3 and 4) or anti-FLAG antibodies (lanes 5 and 6). (B) Anti-T7 antibodies immunoprecipitate T7-tagged RAGE. T7-tagged RAGE constructs were transfected into CHO-CD14 cells, and cell lysates were immunoprecipitated with either anti-T7 (lanes 1 and 2) or anti-RAGE antibodies (lanes 3 and 4), and the precipitants were blotted with anti-RAGE antibodies. To avoid recognition of immunoglobulin from primary antibodies used for IP, mouse anti-T7 and goat anti-RAGE antibodies were used for IP, whereas rabbit anti-RAGE antibodies were used for WB. (C) Anti-FLAG antibodies immunoprecipitate FLAG-tagged RAGE. Mouse anti-FLAG (M2) antibodies were used for IP, and rabbit anti-RAGE antibodies were used for WB.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the nucleotide sequence of a nucleic acid module encoding the hRAGE signal peptide, T7 tag and a multiple cloning site (the "T7 module").

SEQ ID NO: 2 is the amino acid sequence encoded by the T7 module.

SEQ ID NO: 3 is the nucleotide sequence of a nucleic acid module encoding the hRAGE signal peptide, FLAG tag and a multiple cloning site (the "FLAG module").

SEQ ID NO: 4 is the amino acid sequence encoded by the FLAG module.

SEQ ID NOs: 5 and 6 are the nucleotide and amino acid sequences, respectively, of human RAGE (GenBank Accession No. NM_001136, deposited on Oct. 17, 2000).

SEQ ID NOs: 7 and 8 are the nucleotide and amino acid sequences, respectively, of human TLR4 (GenBank Accession No. NM_138554, deposited on Apr. 4, 2002).

SEQ ID NOs: 9 and 10 are the nucleotide and amino acid sequences, respectively, of human AT1 (GenBank Accession No. NM_031850, deposited on May 15, 2001).

SEQ ID NO: 11 is the amino acid sequence of a T7 epitope tag.

SEQ ID NO: 12 is the amino acid sequence of a FLAG epitope tag.

SEQ ID NO: 13 is the amino acid sequence of a HA epitope tag.

SEQ ID NO: 14 is the amino acid sequence of a VSV-G epitope tag.

SEQ ID NO: 15 is the amino acid sequence of a V5 epitope tag.

SEQ ID NO: 16 is the amino acid sequence of a c-myc epitope tag.

SEQ ID NO: 17 is the amino acid sequence of a $His_6$ epitope tag.

SEQ ID NO: 18 is the amino acid sequence of a glycosylation consensus site of human RAGE.

SEQ ID NO: 19 is the amino acid sequence of an enterokinase cleavage sequence.

SEQ ID NOs: 20 and 21 are nucleic acid and amino acid sequences, respectively, of GFP S11. The amino acid sequence of GFP S11 includes a 10-amino acid poly G flexible linker at the C-terminus.

SEQ ID NOs: 22 and 23 are nucleic acid and amino acid sequences, respectively, of GFP S1-10.

SEQ ID NOs: 24 and 25 are nucleic acid and amino acid sequences, respectively, of a GFP S11 that can be used with a three plasmid split GFP system. The amino acid sequence of GFP S11 includes a 10-amino acid poly G flexible linker at the C-terminus.

SEQ ID NOs: 26 and 27 are nucleic acid and amino acid sequences, respectively, of a GFP S10. The amino acid sequence of GFP S10 includes a 10-amino acid poly G flexible linker at the C-terminus.

DETAILED DESCRIPTION

I. Introduction

The expression of mammalian membrane proteins in laboratory cell lines provides a means for characterization and careful dissection of their biological functions. However, it is often difficult to design and generate effective antibodies to membrane proteins for these types of studies. As a result, expressed membrane proteins cannot be detected using common biochemical approaches such as Western blotting, immunoprecipitation, and immunohistochemical analysis.

To circumvent such roadblocks, the inventors designed and generated two representative sets of expression modules that include sequences encoding for three components: (i) a signal peptide from human receptor for advanced glycation end products (RAGE) that targets the intended protein to the endoplasmic reticulum for eventual cell surface expression; (ii) a short, antigenic epitope tag that elicits specific antibody recognition; and (iii) a series of restriction sites that facilitate subcloning of a selected membrane protein. In addition, the modules were designed to confer flexibility of switching the epitope tag to suit specific tagging needs. For example, the epitope tag can be replaced with another type of tag, such as an affinity tag or a fluorescent tag or other type of marker protein or peptide.

The modules were subcloned into expression vectors and successfully tested with both Type I and Type III membrane proteins, including human receptor for advanced glycation end products (hRAGE), human toll-like receptor (TLR) 4, and human angiotensin II receptor 1 (AT1). It is anticipated that the modules provided herein can be used with any type of membrane protein. The expressed membrane proteins can be readily detected by Western blotting and immunoprecipitation with antibodies to their respective epitope tags. In addition, the expressed membrane proteins localize to the cell surface, and maintain their modifications and biological functions. Thus, the nucleic acid modules described herein serve as effective tools that facilitate biochemical studies of membrane proteins.

Further described herein are methods of detecting oligomerization of a membrane protein by combining the disclosed nucleic acid molecules with split GFP bi-molecular fluorescence complementation. To study oligomerization of membrane proteins, the inventors designed vectors that included the coding sequence for beta strands 1-10 of GFP (S1-10), which were complemented with vectors encoding the remaining portion of GFP (S11). Co-transfection of the two vectors, and subsequent membrane protein expression, results in fluorescence only when oligomerization occurs. This method was successfully tested using WT hRAGE and can be used to not only confirm oligomerization of membrane proteins in vivo, but to determine which protein domains are required for oligomerization.

II. Abbreviations

| | |
|---|---|
| AT1 | Angiotensin II receptor 1 |
| BSA | Bovine serum albumin |
| CHO | Chinese hamster ovary |
| CMV | Cytomegalovirus |
| DAPI | 4'-6-diamidino-2-phenylindole |
| DNA | Deoxyribonucleic acid |
| DTT | Dithiothreitol |
| ER | Endoplasmic reticulum |
| GFP | Green fluorescent protein |
| GPCR | G protein-coupled receptor |
| HA | Hemagglutinin |
| HEK | Human embryonic kidney |
| HMGB | High mobility group box |
| hRAGE | Human receptor for advanced glycation end products |
| HRP | Horseradish peroxidase |
| IP | Immunoprecipitation |
| MCS | Multiple cloning site |
| PBS | Phosphate-buffered saline |
| PCR | Polymerase chain reaction |

-continued

| | |
|---|---|
| PMSF | Phenylmethanesulphonylfluoride |
| RAGE | receptor for advanced glycation end products |
| RT-PCR | Reverse transcriptase PCR |
| S1-9 | Beta strands 1-9 of GFP |
| S1-10 | Beta strands 1-10 of GFP |
| S10 | Beta strand 10 of GFP |
| S11 | Beta strand 11 of GFP |
| SDS-PAGE | Sodium dodecyl sulfate-polyacrylamide gel electrophoresis |
| TLR | Toll-like receptor |
| VSV-G | Vesicular stomatitis virus glycoprotein |
| WB | Western blot |

III. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Angiotensin II receptor 1 (AT1): A potent vasopressor hormone and a primary regulator of aldosterone secretion. AT1 is an important effector controlling blood pressure and volume in the cardiovascular system. AT1 may also play a role in the generation of reperfusion arrhythmias following restoration of blood flow to ischemic or infarcted myocardium. At least five transcript variants have been described for this gene. Additional variants have been described but their full-length nature has not been determined. The entire coding sequence is contained in the terminal exon and is present in all transcript variants. The AT1 protein is a seven-transmembrane domain Type III membrane protein. AT1 is also known as angiotensin II receptor, type 1; AGTR1; AG2S; AGTR1A; AGTR1B; AT1B; AT1R; AT2R1; AT2R1A; AT2R1B; HAT1R; angiotensin receptor 1; angiotensin receptor 1B; and type-1B angiotensin II receptor. AT1 sequences, including human sequences and sequences from other species, are known in the art, including GenBank Accession No. NM_031850 (SEQ ID NOs: 9 and 10).

Antibiotic resistance gene: A gene that when expressed, confers resistance to a particular antibiotic. Examples of antibiotic resistance genes include, but are not limited to ampicillin, neomycin, kanamycin and zeocin resistance genes.

Contacting: Placement in direct physical association.

Expression: The process by which the coded information of a gene is converted into an operational, non-operational, or structural part of a cell, such as the synthesis of a protein.

Green fluorescent protein (GFP): As used herein, "GFP" refers to any fluorescent protein that fluoresces green, including fragments, derivatives and variants thereof. For example, derivatives of GFP include enhanced GFP and Emerald. The GFP structure includes eleven anti-parallel outer beta strands and one inner alpha strand. In some embodiments of the compositions and methods disclosed herein, fragments of GFP are used which do not fluoresce on their own, but will fluoresce when in the presence of the remaining fragment or fragments. For example, GFP S1-10 includes beta strands 1-10 and GFP S11 includes beta strand 11. Neither molecule fluoresces alone, but will form the complete fluorophore when brought into association. In other examples, a tripartite system is used that includes GFP S11, GFP S10 (beta strand 10 alone) and GFP S1-9 (beta strands 1-9).

Fluorescent protein: A protein that has the ability to emit light of a particular wavelength when exposed to light of another wavelength. Examples of fluorescent proteins include, but are not limited to green fluorescent protein (GFP), yellow fluorescent protein, blue fluorescent protein, cyan fluorescent protein and red fluorescent protein, and derivatives thereof.

Isolated: An "isolated" biological component (such as a nucleic acid molecule, protein, or cell) has been substantially separated or purified away from other biological components in the cell of the organism, or the organism itself, in which the component naturally occurs, such as other nucleic acid, proteins and cells. Nucleic acid molecules and proteins that have been "isolated" include nucleic acid molecules (such as DNA or RNA) and proteins purified by standard purification methods. The term also embraces nucleic acid molecules and proteins prepared by recombinant expression in a host cell as well as chemically synthesized nucleic acid molecules and proteins. For example, an isolated cell is one that is substantially separated from other types of cells or from an organism.

Membrane protein: A protein that is attached to or associated with the membrane of a cell or organelle. Membrane proteins are generally categorized into five types based on their topology. Type I membrane proteins have a cytoplasmic C-terminus and an extracellular (for plasma membrane proteins) or luminal (for organelle membrane proteins) N-terminus. Subtype Ia proteins have a cleavable signal sequence, whereas subtype Ib proteins do not have signal sequences. Most eukaryotic membrane proteins with a single membrane-spanning regions are Type Ia membrane proteins. Type II membrane proteins have a cytoplasmic N-terminus and an extracellular or luminal C-terminus. Type III membrane proteins have multiple transmembrane domains in a single polypeptide chain. Subtype IIIa proteins have a cleavable signal sequence, whereas subtype IIIb proteins do not have a signal sequence but have an N-terminus exposed on the exterior surface of the membrane. Type IV membrane proteins are anchored to the membrane bilayer by means of one or more covalently attached fatty acid chains or other type of lipid chain, called a prenyl group. Type V membrane proteins are anchored to the membrane bilayer by a glycosylphosphatidyl-inositol (GPI) anchor attached to the C-terminus.

Multiple cloning site (MCS): A MCS is a region of DNA containing a series of unique restriction enzyme recognition sequences. As used herein, a "unique" restriction enzyme recognition sequence is a recognition site that is present only once in the MCS. Vectors and plasmids used for cloning and expression typically contain a MCS to facilitate insertion of a heterologous nucleic acid sequence, such as the coding sequence of a gene of interest. In some embodiments, the nucleic acid modules described herein have a MCS comprising at least two, at least three, at least four, at least five or at least six unique restriction enzyme recognition sites. A MCS is also referred to as a multicloning site.

Nucleic acid module: As used herein, a nucleic acid module is a nucleic acid molecule that can be used for the cloning, expression and tagging of a membrane protein. The nucleic acid modules include a sequence encoding a signal sequence, a sequence encoding a tag, and a multiple cloning site (MCS). A membrane protein of interest can be cloned into the MCS for expression and tagging.

Oligomer: A molecule that includes more than one monomer. "Oligomerization" refers to the process by which two or more monomers associate to form an oligomer.

Operably linked: A first nucleic acid sequence is operably linked with a second nucleic acid sequence when the first nucleic acid sequence is placed in a functional relationship with the second nucleic acid sequence.

Percent identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Res.* 16:10881-10890, 1988; Pearson and Lipman, *Proc. Natl. Acad. Sci. USA* 85:2444, 1988; and Altschul et al., *Nature Genet.* 6:119-129, 1994. The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Receptor for advanced glycation end products (RAGE): The RAGE gene encodes a member of the immunoglobulin superfamily of cell surface molecules. RAGE is a receptor for various molecules, including the amyloidogenic form of serum amyloid A, amyloid-beta protein, members of the S100/calgranulin superfamily and advanced glycation end products. The gene lies within the major histocompatibility complex (MHC) class III region on chromosome 6. Alternative splicing results in two transcript variants encoding different isoforms. The RAGE protein is a Type I membrane protein comprised of three domains designated V (variable domain), C1 and C2 (constant domains). RAGE is also known as advanced glycosylation end product-specific receptor (AGER) and MGC22357. RAGE sequences, including human sequences and sequences from other species, are known in the art, including GenBank Accession No. NM_001136 (SEQ ID NOs: 5 and 6).

Restriction enzyme: A type of enzyme that cleaves double-stranded or single-stranded DNA at specific nucleotide recognition sites (restriction sites). Restriction enzymes are also known as "restriction endonuclease."

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Signal peptide: A short (typically 3-60 amino acids in length) peptide chain that directs the post-translational transport of a protein. The amino acid sequence of a signal peptide directs a protein to a specific organelle, such as the nucleus, mitochondrial matrix, endoplasmic reticulum or peroxisome. Signal peptides are also referred to as targeting signals, signal sequences, transit peptides or localization signals. In some embodiments, the signal peptide of the nucleic acid modules disclosed herein is a signal peptide that directs a protein to the endoplasmic reticulum. In particular examples, the signal peptide is from human RAGE.

Tag: As used herein, a "tag" is an amino acid sequence fused to a heterologous protein that facilitates the detection or isolation of the heterologous protein. Tags contemplated for use with the compositions and methods described herein include, but are not limited to epitope tags, affinity tags and fluorescent proteins. An epitope tag is typically a short amino acid sequence that can be detected using antibodies that specifically recognize the tag. An affinity tag is a polypeptide sequence that specifically binds a substrate (for example, a histidine tag has affinity for nickel). Fluorescent proteins include, for example, GFP. Although tags are often grouped into the aforementioned categories, one of skill in the art will recognize that some tags can be members of more than one group. For example, specific antibodies are available for some types of affinity tags (e.g., a histidine tag), therefore these types of tags can be considered both affinity and epitope tags. In some embodiments, the nucleic acid modules disclosed herein encode an epitope tag, such as T7, FLAG, hemagglutinin (HA) VSV-G, V5 or c-myc. Antibodies to these and other epitope tags are commercially available for a variety of sources. In some embodiments, the tag is an affinity tag, such as a histidine tag (e.g., His$_6$), MBP, CBP or GST. In some embodiments, the tag is a fluorescent protein, such as GFP or enhanced GFP.

Tagging: Refers to the process of recombinantly attaching a tag to a protein of interest, such as to facilitate detection or isolation of the protein.

Toll-like receptor 4 (TLR4): A member of the toll-like receptor (TLR) family which plays a fundamental role in pathogen recognition and activation of innate immunity. TLRs are highly conserved from *Drosophila* to humans and share structural and functional similarities. They recognize pathogen-associated molecular patterns (PAMPs) that are expressed on infectious agents, and mediate the production of cytokines necessary for the development of effective immunity. The TLR4 protein is a Type I membrane protein. TLR4 is also known as TOLL, CD284, hToll and ARMD10. TLR4 sequences, including human sequences and sequences from other species, are known in the art, including GenBank Accession No. NM_138554 (SEQ ID NOs: 7 and 8).

Transfection: Refers to the process of introducing nucleic acid into a cell or tissue. Transfection can be achieved by any of a number of methods, such as, but not limited to, liposomal-mediated transfection, electroporation and injection.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Overview of Several Embodiments

Disclosed herein are nucleic acid modules for expression and tagging of membrane proteins. The modules comprise in the 5' to 3' direction: (i) a nucleic acid sequence encoding the signal peptide of receptor for advanced glycation end products (RAGE); (ii) a nucleic acid sequence encoding a tag; and (iii) a multiple cloning site (MCS). In some embodiments, RAGE is human RAGE (hRAGE). The RAGE signal peptide can also be from other species, such as mouse, rat, bovine or primate species. RAGE sequences from a variety of species are known in the art. In some examples, the RAGE signal peptide is at least 80%, at least 85%, at least 90%, at least 95% or at least 99% identical to residues 1-23 of SEQ ID NO: 2 and maintains the function of directing a newly transcribed protein into the secretory system. In some cases, the signal peptide of RAGE comprises residues 1-23 of SEQ ID NO: 2 or consists of residues 1-23 of SEQ ID NO: 2.

The tag encoded by the nucleic acid module can be any type of protein tag that does not interfere with expression of the protein to which the tag is fused, or targeting to the endoplasmic reticulum. In some embodiments, the tag is an epitope tag. In particular examples, the epitope tag is T7 (such as bacteriophage T7 gp10), FLAG, hemagglutinin (HA), vesicular stomatitis virus glycoprotein (VSV-G), V5 (the C-terminal sequence of the P and V proteins of simian virus 5), histidine (such as His$_6$) or c-myc. Table 1 lists several common epitope tags and their amino acid sequences. Antibodies for detection of common epitope tags are commercially available (such as from Sigma-Aldrich, GenScript and Cell Signaling Technology).

TABLE 1

Representative Epitope Tags

| Epitope Tag | Sequence | SEQ ID NO: |
|---|---|---|
| T7 | MASMTGGQQMGT | 11 |
| FLAG | DYKDDDDK | 12 |
| HA | YPYDVPDYA | 13 |
| VSV-G | YTDIEMNRLGK | 14 |
| V5 | GKPIPNPLLGLDST | 15 |
| c-myc | EQKLISEEDL | 16 |
| His$_6$ | HHHHHH | 17 |

In other embodiments, the tag is an affinity tag. In particular examples, the affinity tag is a histidine tag (such as His$_6$), maltose binding protein (MBP), chitin binding protein (CBP) or glutathione-S-transferase (GST). In other embodiments, the tag is a fluorescent protein. In particular examples, the fluorescent protein is green fluorescent protein (GFP), blue fluorescent protein, yellow fluorescent protein, red fluorescent protein, orange fluorescent protein, cyan fluorescent protein, or derivatives thereof. For example, derivatives of GFP include enhanced GFP and Emerald.

In some examples, the fluorescent tag is a portion of GFP, such as beta strands 1-10 (S1-10), beta strand 10 (S10) or beta strand 11 (S11). In particular examples, the portion of GFP is S1-10 comprising the amino acid sequence of SEQ ID NO: 23; or the portion of GFP is S10 comprising the amino acid sequence of SEQ ID NO: 27; or the portion of GFP is S11 comprising the amino acid sequence of SEQ ID NO: 21 or SEQ ID NO: 25. Examples of split GFP molecules and variants thereof that are suitable for use with the disclosed molecules have been previously described (see, for example, U.S. Pat. No. 7,585,636; U.S. Patent Application Publication No. 2005/0221343; and Cabantous et al., *Nat Biotechnol* 23(1): 102-107, 2005). In some embodiments, the nucleic acid modules comprise a second tag at the 3' end of the module. The second tag also can be any type tag, such as an epitope tag, affinity tag or fluorescent tag. In particular examples, the second tag is an epitope tag, such as T7 or FLAG. A second tag is particularly contemplated for use when the tag located directly 3' of the signal sequence is a portion of a GFP molecule. The second tag allows for efficient detection by Western blot or immunoprecipitation and/or purification (such as by affinity purification).

The MCS can contain any number of unique restriction enzyme recognition sequences. In particular examples, the MCS comprises recognition sites for at least two, at least three, at least four, at least five or at least six different restriction enzymes. In addition, the MCS can include recognition sequences for any desired restriction enzyme. To facilitate cloning of a membrane protein into the MCS, it is advantageous to include a recognition sequence for at least one restriction enzyme that does not have a recognition site in the nucleic acid sequence encoding the membrane protein. In particular examples, the MCS includes recognition sequences for BamHI, KpnI, HindIII, XhoI, XbaI and ApaI. Restriction enzymes and their recognition sequences are well known in the art. For example, restriction enzyme recognition sequences can be found online from New England Biolabs, Inc. (www.neb.com).

In some embodiments disclosed herein, the nucleotide sequence of the nucleic acid module is at least 80%, at least 85%, at least 90%, at least 95% or at least 99% identical to SEQ ID NO: 1 or SEQ ID NO: 3. In particular examples, the nucleotide sequence of the nucleic acid module comprises SEQ ID NO: 1 or SEQ ID NO: 3. In some examples, the nucleotide sequence of the nucleic acid module consists of SEQ ID NO: 1 or SEQ ID NO: 3

In some embodiments, the nucleic acid modules disclosed herein further comprise the coding sequence of a membrane protein inserted into the MCS. The membrane protein can be any protein with a domain that traverses a cellular membrane (such as a Type I, Type II or Type III membrane protein) or is linked to a membrane (such as a Type IV or Type V membrane protein). In some embodiments, the membrane protein is a Type I membrane protein, such as a subtype Ia or subtype Ib protein. In particular examples, the Type I membrane protein is RAGE or TLR4. In some embodiments, the membrane protein is a Type III membrane protein, such as a subtype IIIa or subtype IIIb protein. In particular examples, the Type III membrane protein is AT1. The coding sequence of the membrane protein subcloned into the nucleic acid module does not contain its native signal peptide as the module includes the RAGE signal peptide.

In some embodiments, the nucleic acid molecules further include a sequence encoding a protease cleavage site between the sequence encoding the epitope tag and the MCS. The presence of the cleavage site allows for removal of the epitope tag from the membrane protein (that has been inserted into the MCS) following expression and purification. The sequences of numerous protease cleavage sites are well known in the art and can be included in the disclosed nucleic acid modules. In some examples, the protease cleavage sequence is an enterokinase protease cleavage sequence, such as DDDDK (SEQ ID NO: 19). In other examples, the protease cleave sequence is a thrombin cleavage site.

Also provided herein are vectors comprising the nucleic acid modules disclosed herein. The vector can be any type of vector that is suitable for expression of proteins in a cell. In some embodiments, the vector is a mammalian expression vector, such as a pCDNA vector. In particular examples, the expression vector is pCDNA3.1. In other embodiments, the vector is a viral vector, such as a retroviral vector, an adenoviral vector, an adeno-associated virus vector, a vaccinia virus vector or a herpes simplex virus vector. The vector can further include any elements that facilitate cloning or expression of a nucleic acid sequence, or facilitate maintenance of the vector in a transfected cell. In some embodiments, the vector comprises a promoter, such as a CMV promoter or an SV40 promoter. Promoters for expression in mammalian cells are well known in the art and a suitable promoter can be readily selected by one of ordinary skill. In some embodiments, the vector comprises at least one antibiotic resistance gene. In particular examples, the at least one antibiotic resistance gene is an ampicillin resistance gene, a neomycin resistance gene, a zeocin resistance gene, or a combination thereof. Vectors can further comprise other elements, including an origin of replication or a polyadenylation sequence.

Further provided are isolated cells comprising a nucleic acid module-containing vector as described herein. For example, a vector comprising a nucleic acid module can be transfected into a cultured or primary cell. The vector can be transiently transfected or stably transfected. For stable transfection, cells containing the vector can be selected by growth of the cells in medium containing an appropriate antibiotic (depending on which antibiotic resistance gene the vector contains). In some examples, the cell is a mammalian cell. Mammalian cells suitable for expression of membrane proteins are well known in the art and include, for example, HEK293 cells, CHO cells, HeLa cells and NIH3T3 cells.

Also provided herein is a method of expressing and tagging a membrane protein, comprising cloning the coding sequence of the membrane protein into the MCS of a vector comprising a nucleic acid module described herein. The method can further include transfecting a cell with the vector under conditions sufficient to allow for expression of the membrane protein. Once expressed, the tagged membrane proteins can be detected and/or isolated using standard biochemical techniques, such as the techniques described in the Examples below. For instance, tagged membrane proteins can be detected using antibodies specific for the tag, such as by WB, IP, immunohistochemistry or microscopy. When the tag is a fluorescent protein, detection can be achieved by microscopy. For isolation of membrane proteins from cell extracts, one can use an appropriate affinity column. For example, if the tag is a histidine tag, a nickel column can be used to isolate the membrane protein. If the membrane protein is tagged with an epitope tag, an affinity column containing antibodies specific for the epitope tag can be used to isolate the membrane protein.

V. Membrane-Targeting and Tagging Membrane Proteins

Membrane proteins constitute about 30% of the entire protein content of cells, and function in various cellular events including solute and ion transport, energy and sensory stimuli transduction, and information processing. They participate in the development of many human diseases and hence are major pharmacological intervention targets. Despite the important role of many membrane proteins, these proteins remain poorly studied. The recombinant expression of mammalian membrane proteins has been a major stumbling block in efforts to dissect their biological function and determine their structure (White, *Protein Sci* 13:1948-1949, 2004). One existing obstacle is the lack of effective antibodies to membrane proteins for detection. The expression modules described herein for tagging cloned mammalian membrane proteins provide an effective means to overcome prior obstacles.

Figure 5A:
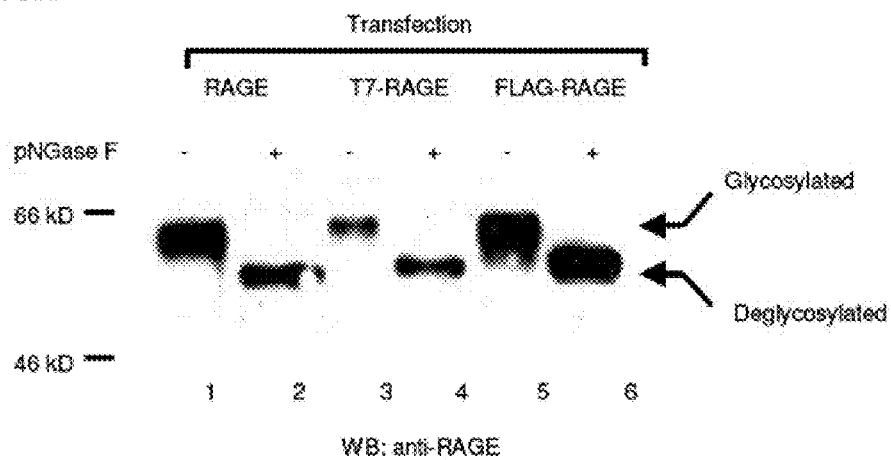
FIGS. 5A-5C show glycosylation of tagged RAGE and TLR4 by WB. Tagged and untagged RAGE and TLR4 were expressed in CHO-CD14 cells. Cell lysates were treated with pNGase F at 37° C. for 1 hour and resolved with SDS-PAGE. (A) WB of untagged RAGE (lanes 1 and 2), T7-RAGE (lanes 3 and 4) or FLAG-RAGE (lanes 5 and 6) using anti-RAGE antibody. (B) WB of tagged RAGE with either anti-T7 (lanes 1 and 2) or anti-FLAG (lanes 3 and 4) antibodies. (C) WB of TLR4 with either anti-T7 (lanes 1 and 2) or anti-FLAG (lanes 3 and 4) antibodies.

The membrane-targeting and tagging modules disclosed herein are designed to possess versatility that adapts to various tagging and subcloning needs. The cleavage of the RAGE signal peptide from the mature RAGE protein occurs between amino acids 23 (alanine, A) and 24 (glutamine, Q). In particular examples described herein, to ensure that the signal peptide is still cleavable when linked to the tag sequence, the restriction sequence of EcoRI (GAA TTC) was used as the link. The insertion of this restriction site results in a glutamic acid (E) as the residue adjacent to the 23rd residue of the signal peptide. The A-E juncture sufficiently mimics the natural A-Q juncture to allow for a successful proteolytic cleavage within the ER (von Heijne, *Eur J Biochem* 133:17-21, 1983). Although the N-termini of the tagged proteins were not sequenced to verify the cleavage of the signal peptide, the finding that the tagged proteins are correctly localized at the cell surface and correctly modified (FIGS. 4, 5 and 7) indicates that the designed modules do not interfere with the normal biogenesis of the tagged membrane proteins. The universal adaptation of mammalian membrane proteins into the disclosed modules can be achieved by amplification of the coding sequences of the target mature membrane protein by PCR, using a pair of primers flanked with the chosen restriction sequences from the MCS (see FIG. 1).

Based on their topology, integral membrane proteins are divided into five classes (Chou and Elrod, *Proteins* 34:137-153, 1999). Both Type I and II membrane protein are bitopic, with Type I proteins exposing their N-terminal portion on the extracellular side of the membrane, and Type II proteins exposing their C-terminal portion on the extracellular side of the membrane. As demonstrated in FIG. 7, the modules disclosed herein can also be applied to polytopic Type III membrane proteins, which have their N-termini exposed at the extracellular side of the plasma membrane. The other two classes of membrane proteins, lipid chain-anchored and glycosylphosphatidylinositol (GPI)-anchored membrane proteins, are monotopic. Both types also contain signal peptides, and their C-termini are often modified to anchor them to the membrane bilayer (Resh, *Nat Chem Biol* 2:584-590, 2006; Paulick and Bertozzi, *Biochemistry* 47:6991-7000, 2008), thus it is believed that tagging at the N-terminus is also possible for these types of membrane proteins. Given that tagging at the N-terminus is unlikely to interfere with post-translational modifications and localization, it is contemplated herein to apply the disclosed modules to membrane-anchored proteins.

As disclosed herein, no significant cytotoxicity was encountered by expression of any of the three tested membrane proteins (RAGE, TLR4 and AT1). In addition, glycosylation and ligand-binding of the tagged receptors also appeared to be normal. Since adapting other membrane proteins to the designed modules described herein requires a relatively simple subcloning process, and the subsequent Immunodetection of the cloned membrane protein is effective, post-translational modifications and ligand-binding capacity of the target membrane protein can be readily tested, and its biological functions and cellular behaviors can hence be well studied in a common laboratory cell line.

In addition to transient expression in laboratory mammalian cell lines, the designed modules and vectors containing the modules can be used for multiple applications. For example, the subcloned constructs can be used to establish cell lines that stably express the tagged membrane proteins, using antibiotic selection according to the drug-resistance marker included in the vector. The membrane targeting and tagging module can also be subcloned into viral vectors for more efficient delivery, and expression in a wider range of mammalian cell types. Further, the module can be used to generate transgenic animals for physiological and pathological analysis, aided by an effective antibody to the tag.

VI. Oligomerization of Membrane Proteins

The use of self-assembling GFP fragments has been described for tagging and detection of proteins (Cabantous et al., *Nat Biotechnol* 23(1):102-107, 2005; U.S. Pat. No. 7,585,636; and U.S. Patent Application Publication No. 2005/0221343). This system is referred to as split GFP bimolecular fluorescence complementation, or simply "split GFP." The principle behind the split GFP system is that one portion of GFP is fused to a protein of interest, and the remainder of GFP is expressed separately (either alone or fused to another protein). Neither fragment alone is fluorescent. However, when the two fragments of GFP are mixed, the fragments associate, resulting in GFP folding and formation of the fluorophore. Typically, one fragment of GFP includes beta strand 11 (referred to herein as S11) and the other fragment contains beta strands 1-10 (S1-10). Exemplary S11 and S1-10 nucleic acid and amino acid sequences are set forth herein as SEQ ID NOs: 20-25. GFP fragment variants have also been designed that result in improved folding and stability (Cabantous et al., *Nat Biotechnol* 23(1):102-107, 2005; U.S. Pat. No. 7,585,636; and U.S. Patent Application Publication No. 2005/0221343).

Disclosed herein is a method of detecting oligomerization of a membrane protein by incorporating the split GFP system into the membrane protein expression modules described herein. To evaluate oligomerization of membrane proteins, vectors were designed that included GFP S11 as the epitope tag, located between the RAGE signal sequence and the MCS (or membrane protein cloned into the MCS). A second set of vectors were designed that utilize S1-10 as the epitope tag. Both types of vectors include a membrane protein cloned into the MCS. By co-transfecting the two types of vectors, oligomerization of the encoded membrane protein can be detected. This system can further be used to identify domains in a membrane protein that are required for oligomerization. For example, one set of vectors can include the wild-type protein and the second set of vectors can include deletion mutants of the protein. The absence of fluorescence when a deletion mutant is used indicates the deleted domain is required for oligomerization.

Thus, in some embodiments, provided is a method of detecting oligomerization of a membrane protein by:

(i) transfecting a cell with a first vector and a second vector, wherein the first vector comprises (a) a nucleic acid sequence encoding the signal peptide of RAGE; (b) a nucleic acid sequence encoding GFP fragment S11; and (c) a nucleic acid sequencing encoding the membrane protein, and wherein the second vector comprises (a) a nucleic acid sequence encoding the signal peptide of RAGE; (b) a nucleic acid sequence encoding GFP fragment S1-10; and (c) a nucleic acid sequencing encoding the membrane protein, wherein the vectors are transfected under conditions sufficient to allow for expression of the membrane protein; and (ii) detecting the presence or absence GFP fluorescence in the cell, wherein the presence of GFP fluorescence indicates that the membrane protein has oligomerized.

In some examples, the first or second vector comprises a nucleic acid sequence encoding a fragment or deletion mutant of the membrane protein. In some examples, the first and/or second vector further comprises a nucleic acid sequence encoding a second tag, such as an epitope tag or affinity tag, at the 3' end of the module (3' of the nucleic acid sequence encoding the membrane protein).

In alternative embodiments, a two-vector system is used in which the first vector encodes GFP S11 and the second vector encodes GFP S10 (beta strand 10 only). Purified GFP S1-9 is then added to allow for formation of the fluorophore. Thus, fluorescence depends on not only oligomerization of the membrane proteins encoded by the first and second vectors, but requires the addition of GFP S1-9. This tripartite system avoids automatic interactions between GFP S11 and GFP S1-10 that sometimes occurs due to overexpression. Representative GFP S10 and S11 sequences for use with this system are provided as SEQ ID NOs: 24-27.

Thus, in one embodiment, provided is a method of detecting oligomerization of a membrane protein, comprising:

(i) transfecting a cell with a first vector and a second vector, wherein the first vector comprises (a) a nucleic acid sequence encoding the signal peptide of RAGE; (b) a nucleic acid sequence encoding GFP fragment S11; and (c) a nucleic acid sequencing encoding the membrane protein, and wherein the second vector comprises (a) a nucleic acid sequence encoding the signal peptide of RAGE; (b) a nucleic acid sequence encoding GFP fragment S10; and (c) a nucleic acid sequencing encoding the membrane protein, wherein the vectors are transfected under conditions sufficient to allow for expression of the membrane protein;

(ii) contacting the transfected cell with purified GFP S1-9; and (ii) detecting the presence or absence GFP fluorescence in the cell, wherein the presence of GFP fluorescence indicates that the membrane protein has oligomerized.

In some examples, the first or second vector comprises a nucleic acid sequence encoding a fragment or deletion mutant of the membrane protein. In some examples, the first and/or second vector further comprises a nucleic acid sequence encoding a second tag, such as an epitope tag or affinity tag, at the 3' end of the module (3' of the nucleic acid sequence encoding the membrane protein).

The following examples are provided to illustrate certain particular features and/or embodiments. These examples should not be construed to limit the disclosure to the particular features or embodiments described.

EXAMPLES

Example 1

Material and Methods

This example describes the experimental procedures for the studies described in Examples 2-6.

Enzymes, Chemicals and Antibodies

All restriction enzymes, T4 Quick DNA ligase, T4 DNA ligase, PNGase F, vent DNA polymerase, and other PCR reagents were purchased from New England Biolabs (Beverly, Mass.). Chemicals used for buffers were from Fisher Scientific Company (Pittsburgh, Pa.). Rabbit anti-RAGE (H-300) and anti-AT1 antibodies (N-10) were purchased from Santa Cruz Biotechnology, Inc. (Santa Cruz, Calif.); mouse anti-FLAG (M2, and M2-peroxidase conjugate) antibodies were from Sigma-Aldrich Company (St. Louis, Mo.); mouse anti-T7 tag antibodies were from Novagen-EMD (Gibbstown, N.J.); rabbit anti-T7 tag antibodies were from Chemicon-Millipore (Billerica, Mass.); mouse anti-TLR4 antibodies were from Imgenex Corp. (San Diego, Calif.); and anti-HA (3F10, Rat, peroxidase conjugate, and mouse unconjugated) antibodies were from Roche Applied Science (Indianapolis, Ind.).

Construction of Signal Peptide-Epitope Tag-MCS Module

The coding sequence of human RAGE signal peptide (23 amino acids) was amplified by PCR from a RAGE clone (Origene, Rockville, Md.) with primers flanked with a 5' SpeI site and a 3' EcoRI site. This PCR fragment was ligated to synthetic epitope tag sequences flanked with 5' EcoRI, and 3' BamHI site with T4 Quick DNA ligase at room temperature for 10 minutes, and the ligated signal peptide-epitope tag fragment was amplified by PCR with a 5' primer to the signal peptide sequences, and a 3' primer to the epitope tag. The resultant fragment was then ligated to the NheI and BamHI sites in pCDNA3.1 (zeo+) or pCDNA3.1 (neo+) (Invitrogen). The NheI-SpeI ligation results in the sequence GCTAGT, which is uncleavable by either NheI or SpeI restriction enzymes and hence "fix" the signal peptide sequences to the vector. Synthetic multiple cloning site (MCS) sequences were subsequently inserted between BamHI and XbaI sites to complete the module. The entire module was nucleotide-sequenced to confirm the authenticity.

Subcloning of Membrane Proteins

Full-length RAGE was cloned from the human monocyte cell line U937 (ATCC, Manassas, Va.) by RT-PCR using primers specific to RAGE. Full-length human RAGE, TLR4 and AT1 cDNA were used as templates for PCR. The coding sequences of mature membrane proteins were amplified by PCR and inserted between BamHI and XbaI sites in the designated vector. For RAGE subcloning, a BglII site was used to ligate to the BamHI site in the vector to avoid internal cleavage of the RAGE cDNA sequence by BamHI. All constructed expression vectors carrying the membrane proteins were nucleotide-sequenced and confirmed.

Culture and Transfection of Laboratory Cell Lines

CHO-CD14 cells (Kirkland et al., *J. Biol. Chem.* 268(33): 24818-24823, 1993) were cultured in RPMI 1640 medium supplemented with 10% fetal bovine serum (ATCC). HEK 293 cells were obtained from ATCC, and were cultured in DMEM medium supplemented with 10% fetal bovine serum (Invitrogen). For Western blotting and immunoprecipitation, $5 \times 10^5$ to $1 \times 10^6$ CHO-CD14 cells were seeded on 35 mm plates the day before transfection, and LIPOFECTAMINE™ or LIPOFECTAMINE™ 2000 (Invitrogen) were used to transfect CHO-CD14, according to the manufacturer's instructions. For each transfection, 1-1.5 µg DNA was used. For immunostaining, $6 \times 10^4$ HEK293 cells were seeded in 4-well glass chamber slides one day before transfection, and 1.25 µg of plasmid DNA was used.

Western Blotting and Immunoprecipitation

The transfected cells were incubated at 37° C. overnight, washed with 1× phosphate buffered saline (PBS), and lysed with 250 µl ELB buffer (50 mM Tris, pH 7.5, 300 mM NaCl, 0.1% Nonidet-P40, 5 mM ethylenediaminetetraacetic acid, 1 mM phenylmethanesulphonylfluoride (PMSF), 1 mM dithiothreitol (DTT), and protease inhibitor cocktail (Sigma-Aldrich)) for 30 minutes. The lysates were rotated at 4° C. for 1-2 hours to extract membrane proteins, and were centrifuged at 14,000 rpm for 30 minutes to obtain supernatants for further assays. Protein concentration of the lysates was determined with the BCA protein assay kit from Pierce-Thermo Company (Rockford, Ill.) and 0.5-1 µg of the total protein was used for Western blotting analysis as described previously (Lin et al., *Cell* 92:819-828, 1998; Fu et al., *J Biol Chem* 279:12819-12826, 2004). Immunoprecipitation was also described previously (Lin et al., *Cell* 92:819-828, 1998; Fu et al., *J Biol Chem* 279:12819-12826, 2004), and total supernatants were used.

Ligand-Binding Assays

Crude membrane was prepared from RAGE-transfected CHO-CD14 cells as follows. The cells were rinsed with 1×PBS and swelled in chilled low ionic buffer (10 m Tris, pH 7.5, 0.2 mM EDTA, 1 mM PMSF, 1 mM DTT and protease inhibitor cocktail) for 30 minutes. After swelling, the cells were scrapped from the plates and sonicated. The lysates were then centrifuged at 1,500×g for 10 minutes, and the supernatants were transferred into new tubes. The supernatants were supplemented with $Na_2CO_3$ to a final concentration of 0.1 M, and crude membrane was pelleted at 45,000×g for 30 minutes. The obtained membrane was carefully rinsed with 1×PBS, suspended in the same buffer, and frozen for future studies. Cell lysates from HA-high mobility group box (HMGB) 1 transfected cells were prepared as described in the previous section, and incubated with crude membrane preparations at room temperature for 1 hour. Membrane-HMGB 1 mixtures were then immunoprecipitated with antibodies to the epitope tag, and the precipitants were resolved with 4-12% gradient gel (Invitrogen). Western blotting analyses were carried out with either anti-HA, or anti-FLAG and anti-T7 antibodies.

Immunohistochemical Analysis

Transfected cells in chamber slides were rinsed with 1×PBS and fixed in 10% formaldehyde for 15 minutes at room temperature. After fixation, the cells were washed 3 times with 1×PBS and blotted with 1% bovine serum albumin (BSA) in 1×PBS for 30 minutes prior to incubation with primary antibodies in 1% BSA buffer overnight at 4° C. The next day, the cells were washed with 1×PBS, and incubated with either rabbit anti-mouse, or swine anti-rabbit IgG secondary antibodies (Dako North America, Inc., Carpinteria, Calif.) in 1% BSA buffer for 60 minutes at room temperature. Following the secondary antibody incubation, the cells were washed with 1×PBS and incubated with 4'-6-diamidino-2-phenylindole (DAPI) for 1 minute for nuclear staining. Finally, the slides were rinsed with 1×PBS and mounted with mounting medium (Vector Laboratories Inc., Burlingame, Calif.). Immunohistochemical analyses were carried out with LSM-510 confocal microscope (Zeiss).

Example 2

Expression Module Design

This example describes the design of four membrane protein expression modules having either a FLAG or T7 epitope tag.

The membrane protein expression modules were designed to include three components: (1) a sequence encoding the 23-residue signal peptide from human RAGE; (2) the coding sequence of either bacteriophage T7 gp10 (12-residue) or FLAG epitope tag (8-residue); and (3) a multiple cloning site (MCS). The tag was linked to the signal peptide with an EcoRI site (GAA TTC) that adds two amino acids (Glu and Phe). Restriction sequences within the MCS are arranged in tandem of hexamer without additional nucleotide insertions to ensure that inserted target sequences will be in the same reading frame with the preceding signal peptide and the epitope tag. In addition to providing a variety of cloning sites, this arrangement also allows flexibility for the replacement of the epitope tag to suit the specific need. The tag sequence can be synthesized to replace the existing one with its 5' flanked with an EcoRI, and 3' with a restriction sequence of choice within the MCS. The entire module was then subcloned into either pCDNA3.1 vector with a neomycin or zeocin resistance marker. A constitutively active promoter from human cytomegalovirus (CMV) in these vectors drives the expression of the tagged membrane protein in mammalian cells. The map of the designed modules is shown in FIG. 1, and the corresponding vectors summarized in Table 2.

TABLE 2

Expression vectors that harbor designed membrane targeting and epitope-tagging modules

| Vector name | Backbone | Epitope tag | Antibiotic resistance[1] | Size (base pairs) |
|---|---|---|---|---|
| pJP001 | pCDNA3.1 | FLAG | neomycin | 5473 |
| pJP002 | pCDNA3.1 | T7 | neomycin | 5485 |
| pJP007 | pCDNA3.1 | FLAG | zeocin | 5060 |
| pJP008 | pCDNA3.1 | T7 | zeocin | 5072 |

[1]All vectors contain an ampicillin resistance gene

Example 3

Type Ia Membrane Proteins are Successfully Expressed with Designed Modules

This example describes the finding that two Type Ia membrane proteins, RAGE and TLR4, can be efficiently tagged and expressed in mammalian cells using the disclosed membrane protein modules.

Figure 2B:
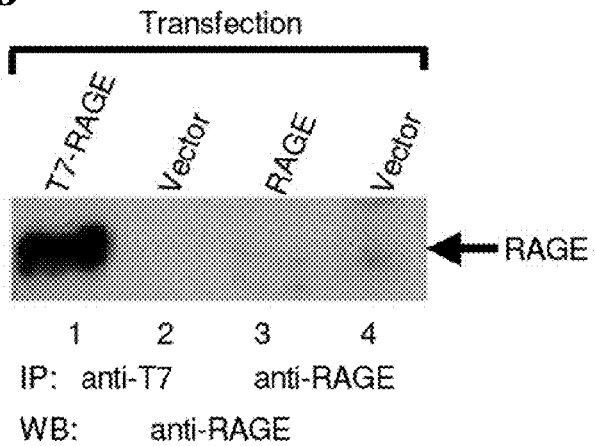
Figure 2C:
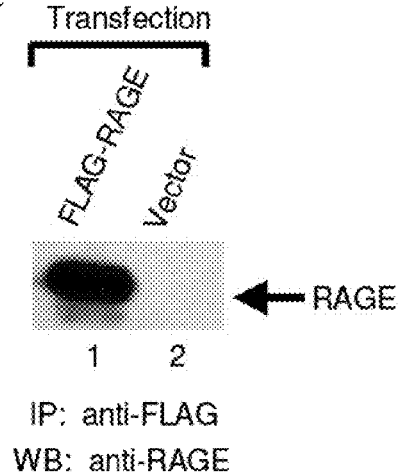

To test whether the designed module can successfully tag and express Type Ia membrane proteins in mammalian cells, human RAGE was selected for testing. The coding sequence of the mature form of RAGE (starting from residue 24) was amplified by PCR and subcloned into vectors pJP007 (FLAG tag) and pJP008 (T7 tag). The expression vectors carrying the test protein were then transfected into CHO-CD14 cells, and cell lysates were prepared for SDS-PAGE, followed with Western blotting. As shown in FIG. 2, either anti-FLAG or anti-T7 antibodies readily detect tagged RAGE proteins, suggesting that the RAGE signal peptide is cleaved correctly within the ER, and the integrity of the epitope tag is maintained. Although the commercial anti-RAGE antibody detects RAGE in Western blotting, it does not immunoprecipitate RAGE, suggesting that this anti-RAGE antibody is unable to bind sufficiently tight to the natural form of RAGE. Both anti-T7 and anti-FLAG antibodies successfully immunoprecipitated tagged RAGE, demonstrating that this tagging strategy can be employed to study the in vivo interactions of this membrane protein with other cellular proteins.

Figure 3A:
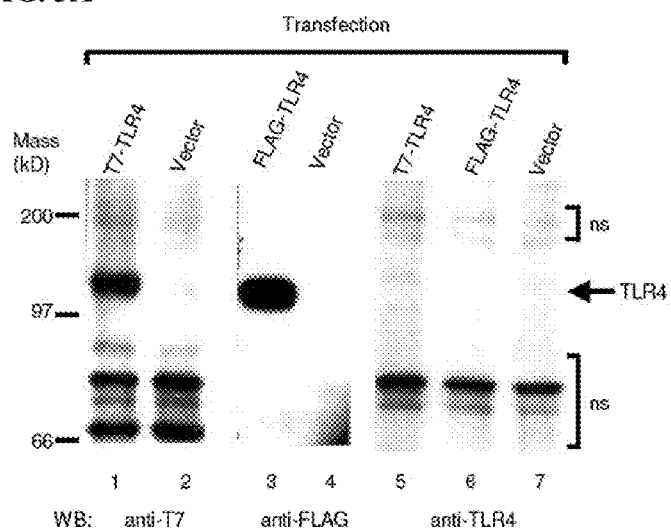
FIGS. 3A-3C show tagged human TLR4 is expressed and detected by antibodies to the epitope tags by WB and IP. Human TLR4 was subcloned into vectors carrying epitope modules and expressed in CHO-CD 14 cells. Cell lysates were prepared and resolved by 4-12% Bis-Tris SDS-PAGE. (A) Antibodies to T7 and FLAG epitope tags detect the expressed TLR4 by WB (ns=non-specific). (B) Immunoprecipitation of T7-TLR4 by anti-T7 antibodies. Transfected cell lysates were immunoprecipitated with rabbit anti-T7 antibodies and Western blotted with mouse anti-T7 antibodies. (C) Immunoprecipitation of FLAG-TLR4 by anti-FLAG antibodies. FLAG-tagged TLR4 was expressed in CHO-CD14 cells and cell lysates were immunoprecipitated with mouse anti-FLAG (M2) antibodies and Western blotted with mouse anti-FLAG antibodies conjugated to horseradish peroxidase (HRP).
Figure 3B:
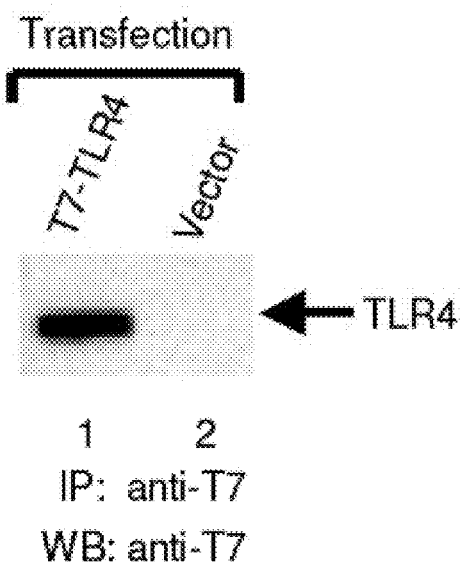
Figure 3C:
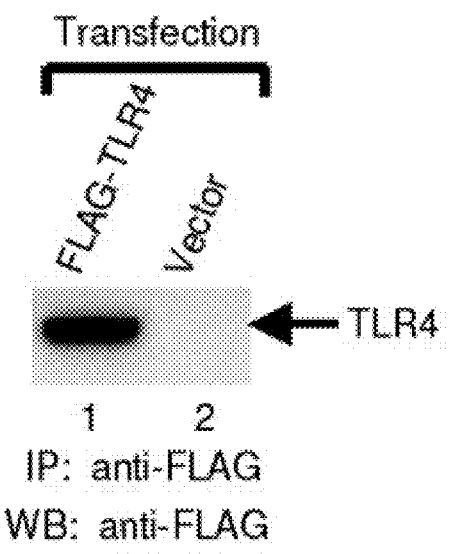

To test whether the designed module can be applied to Type Ia membrane proteins other than RAGE, another Type Ia membrane protein, human TLR4, was evaluated. TLR4 has a higher molecular mass than RAGE. The mature portion of TLR4 (starting from residue 25) was amplified by PCR, and subcloned into pJP007 and pJP008 vectors. The resultant constructs were then transfected and expressed in CHO-CD14 cells. While anti-TLR4 antibodies were unable to detect the expressed TLR4 in cell lysates, both anti-FLAG and anti-T7 antibodies readily detected the tagged TLR4 in Western blot (see FIG. 3). Similar to the tagged RAGE, both anti-FLAG and, anti-T7 antibodies also successfully immunoprecipitated tagged TLR4. Together, these results demonstrate that, subcloned into the designed modules, Type Ia membrane proteins can be successfully expressed in laboratory cell lines with the addition of an effective epitope tag at their N-termini.

Example 4

The Epitope-Tagged Type Ia Membrane Proteins are Expressed at Cell Surface

Since tagged RAGE and TLR4 were extracted from unfractionated cell lysates for Western blotting studies, it is unclear whether the expressed proteins were correctly localized at the cell surface. To examine the localization of expressed Type I membrane proteins, the tagged RAGE and TLR4 were transfected into HEK293 cells, and immunohistochemical analyses were performed with confocal microscopy. As shown in FIG. 4, both tagged RAGE and TLR4 are predominantly expressed at the cell surface, suggesting that tagging will not affect cellular localization of Type Ia membrane proteins.

Example 5

Figure 5B:
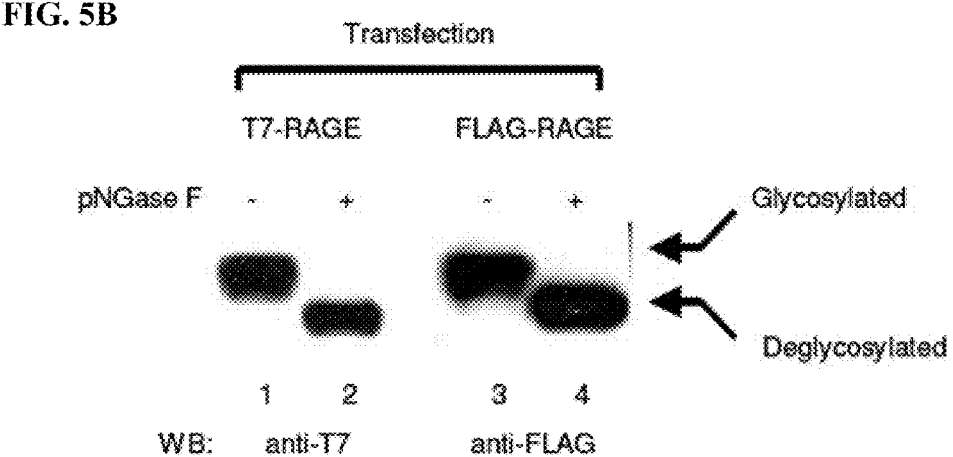
Figure 5C:
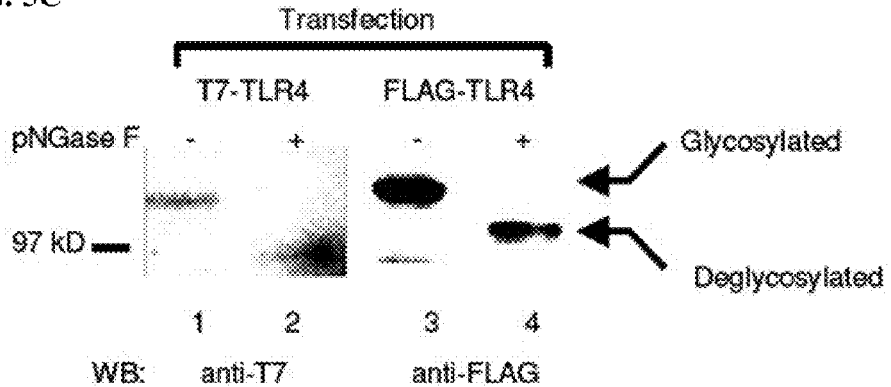

The Epitope-Tagged Type Ia Membrane Proteins are Glycosylated and Maintain their Biological Functions Mammalian membrane proteins are universally glycosylated, which is often necessary to retain their biological functions (Lis and Sharon, *Eur J Biochem* 218:1-27, 1993; Spiro, *Glycobiology* 12:43 R-56R, 2002; Molinari, *Nat Chem Biol* 3:313-320, 2007). Both RAGE and TLR4 contain two putative N-glycosylation sites (i.e. NXS/T, X represents any amino acid), and one of the glycosylation consensus sites of RAGE is located at the second residue of the mature protein (QNIT; SEQ ID NO: 18), in the vicinity of the N-terminal epitope tag. To test whether tagging interferes with this post-translational modification, lysates prepared from transfected CHO-CD14 cells were treated with *Flavobacterium menigosepticum* N-glycosidase (PNGase F) that cleaves glycan chains from membrane proteins. Similar to untagged RAGE, both FLAG-, and T7-tagged RAGE showed mobility shift on SDS-PAGE detected by anti-RAGE antibodies (FIG. 5A), suggesting that tagging does not interfere the N-glycosylation of RAGE. Parallel results were obtained from the tagged TLR4 (FIG. 5B).

Figure 6A:
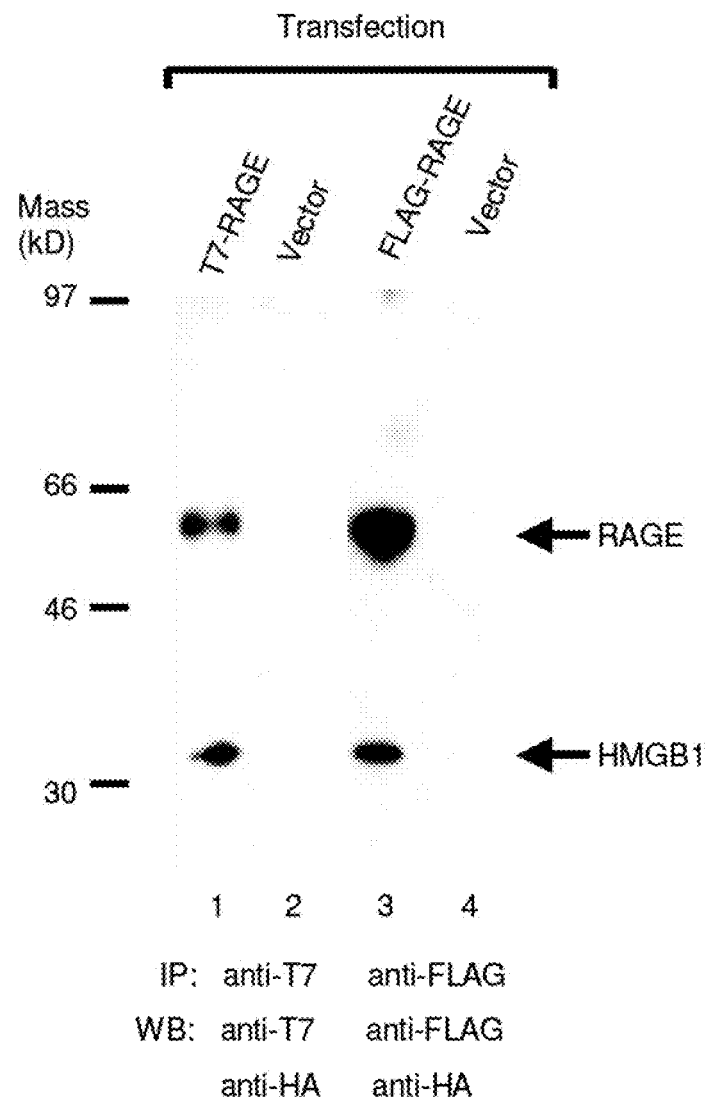
FIGS. 6A-6B are images of WB and IP assays showing tagged RAGE binds its ligand high mobility group box 1 (HMGB1). Hemagglutinin (HA)-tagged HMGB1 was expressed in CHO-CD14 cells. The cell lysates were prepared as described in Example 1. Cells transfected with tagged RAGE were incubated with HA-HMGB1 and crosslinked with DTSSP (2 mM). After crosslinking, the cells were lysed and immunoprecipitated with antibodies to the tag. The precipitants were cleaved in lithium dodecyl sulfate loading buffer containing 200 mM DTT at 80° C. for 10 minutes before being subjected to SDS-PAGE. (A) WB of immunoprecipitants with anti-T7 and anti-HA antibodies (lanes 1 and 2). Rabbit anti-T7 antibodies were used for IP, and mouse anti-T7 and rat anti-HA (3F10, HRP conjugate) were used for WB. Mouse anti-FLAG (M2) antibodies were used for IP, and mouse anti-FLAG (M2, HRP conjugate) and rat anti-HA (3F10, HRP conjugate) were used for WB (lanes 3 and 4). (B) WB to detect HA-HMGB1 input using an anti-HA antibody (3F10, HRP conjugate).
Figure 6B:
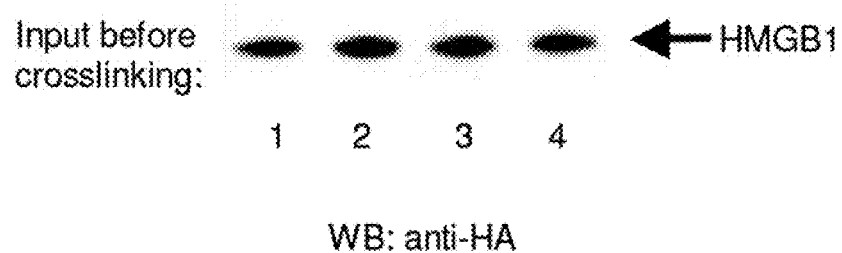

It was further tested whether the tagged RAGE still binds its ligand, HMGB1. Crude membrane fractions were prepared from RAGE-transfected CHO-CD14 cells, and were incubated with HA-HMGB1-transfected cell lysates. After incubation, anti-tag antibodies were used to immunoprecipitate tagged RAGE, and the precipitants were resolved with SDS-PAGE and immunoblotted with anti-HA antibodies. As shown in FIG. 6, both anti-FLAG and anti-T7 antibodies co-immunoprecipitate HMGB1, demonstrating that the tagged receptors maintain their ability for ligand binding. Together, these results suggest that epitope-tagging at the N-terminus of a Type I membrane protein does not affect its post-translational modifications, or its biological functions.

Example 6

The Designed Vectors Tag and Enhance the Expression of Type III Membrane Proteins This example describes the finding that a Type III membrane protein, AT1, is successfully tagged and expressed in mammalian cells using the disclosed modules.

Type III membrane proteins have multiple transmembrane domains in a single polypeptide chain. This group is further divided into two subtypes: Type IIIa membrane proteins contain cleavable signal peptide sequences, whereas those in Type IIIb are synthesized without signal peptides (Singer, *Annu Rev Cell Biol* 6:247-296, 1990). How Type IIIb membrane proteins are translocated to the plasma membrane remains unclear. G protein-coupled receptors (GPCR) are the major drug intervention targets, and among GPCRs, many belong to the Type IIIb membrane protein class. It has been demonstrated that converting a Type IIIb membrane protein, β2-adrenergic receptor, into a Type IIIa by introducing a cleavable signal peptide sequence at its N-terminus, enhances the expression of the receptor (Guan et al., *J Biol Chem* 267:21995-21998, 1992). Here it is tested whether the designed modules can also effectively express human angiotensin II receptor 1 (AT1), a Type IIIb GPCR.

The coding sequence of human AT1 was subcloned into pJP007 and pJP008 vectors, and the resultant constructs were transfected into CHO-CD14 cells for expression. Although commercial anti-AT1 antibodies were effective for immunohistochemical analysis (FIG. 7C), they did not detect AT1 from cell lysates in Western blotting, nor did they immunoprecipitate AT1. Tagged AT1 is readily detected, or immunoprecipitated by either anti-T7 or anti-FLAG antibodies (FIGS. 7A and B). Anti-tag antibodies also detect expressed AT1 at the cell surface (FIG. 7C). Together, these results suggest that, like Type I membrane proteins, the designed module can also effectively tag and express Type IIIb membrane proteins in laboratory cell lines.

Example 7

Split GFP Technology to Monitor RAGE Oligomerization

This example uses split GFP bi-molecular fluorescence complementation (Cabantous et al., *Nat. Biotechnol.* 23(1): 102-107, 2005) to demonstrate that RAGE exists as an oligomer in vivo.

Figure 8:
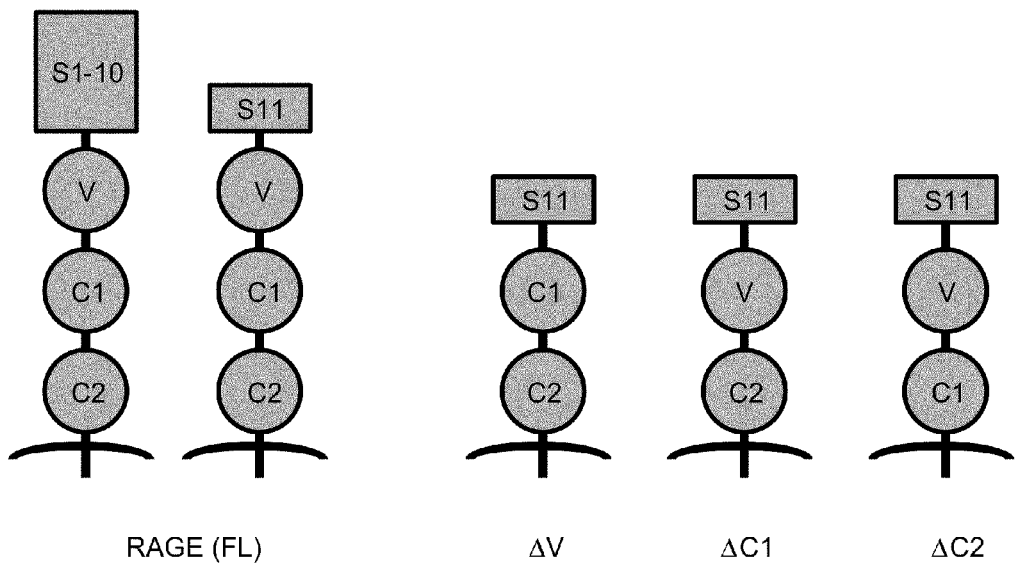
FIG. 8 is a schematic showing the domain structure of WT hRAGE tagged with spGFP S1-10 and spGFP S11, and three hRAGE deletion mutants (ΔV, ΔC1 and ΔC2) tagged with spGFP S11.

Deletion Mutants hRAGE deletion mutants lacking either the V domain (ΔV), C1 domain (ΔC1) or C2 domain (ΔC2) were generated by PCR amplification (see FIG. 8). For the ΔV deletion mutant, amino acids 23-132 of hRAGE (SEQ ID NO: 6) were removed. The ΔC1 and ΔC2 mutants lack amino acids 121-233 and 235-327 of hRAGE (SEQ ID NO: 6), respectively, and each contain an XhoI site (resulting in the amino acids Leu and Glu) to connect the remaining C1 or C2 domain to the V domain. The amplified PCR fragments were digested with BglII and XbaI and the spGFP S11 vector (Cabantous et al., *Nat Biotechnol* 23(1):102-107, 2005) was digested with BamHI and XbaI. Following purification, the restriction enzyme digested PCR fragments were ligated to the purified vector fragments at 16° C. overnight. The ligation mixture was used to transform DH5α competent cells, and the transformed colonies were screened for the correct constructs by restriction mapping. Each mutant was tagged at the N-terminus with spGFP S11, and at C-terminus with the T7 epitope tag (FIG. 9). The constructs were verified by nucleotide sequencing, and a glycerol stock was generated for each mutant clone. Large quantities of plasmid DNA was purified using Qiagen MAXI columns. Expression of the RAGE deletion mutants was verified by transiently expressing them in CHO-CD14 cells and Western blotting the SDS-PAGE resolved cell lysates with anti-T7 antibodies.

Bi-Fluorescence Complementation (Bi-FC)

After overnight incubation at 37° C., transfected cells were examined under a fluorescent microscope and photographed. The transfected cells were subsequently lysed and membrane proteins were extracted. Protein concentration of the lysates was determined with a Pierce kit, and protein samples were resolved with an SDS-PAGE (4-12% Bis-Tris) gel. The resolved gel was transferred to Immobilon-P membrane, and Western blotting was performed using anti-RAGE (to WT) or anti-T7 (to mutants) antibodies. For confocal studies, HEK 293 cells were transfected similar to CHO-CD14 cells and examined using confocal microscopy. Each spGFP S11-tagged hRAGE or hRAGE deletion mutant was co-transfected with spGFPS1-10 tagged hRAGE (WT) to CHO-CD14 cells, using Lipofectamine. Split GFP technology can be used to determine whether oligomerization of a protein occurs because fluorescence only occurs when strands 1-10 (S1-10) and strand 11 (S11) of GFP are brought together. In this present case, detection of fluorescence indicates that WT hRAGE (tagged with S1-10) has oligomerized with either the full-length hRAGE or a deletion mutant of hRAGE (tagged with S11).

Results

Figure 10:
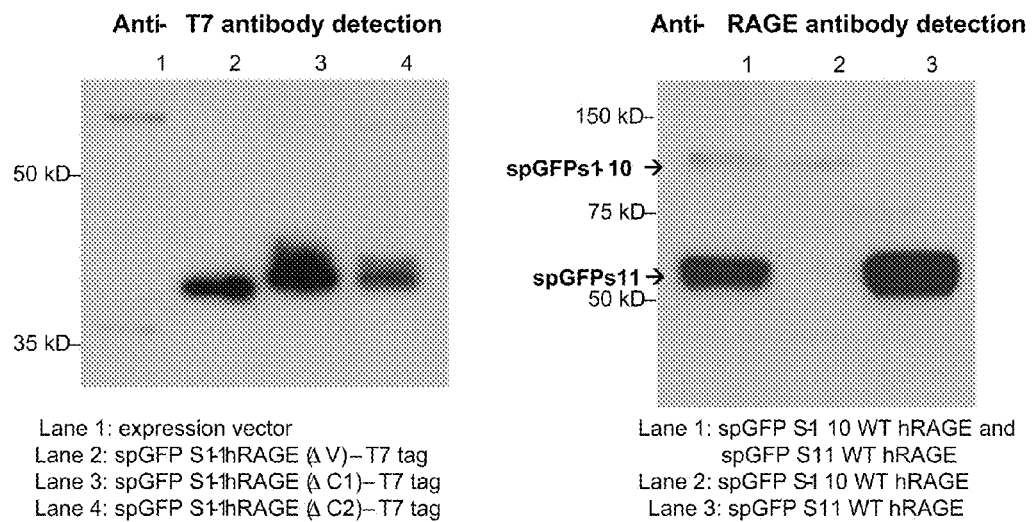
FIG. 10 shows detection of expression of WT hRAGE and hRAGE deletion mutants by Western blot using anti-T7 (for detection of deletion mutants) or anti-RAGE antibody (for detection of WT hRAGE). The results demonstrate proper protein expression for WT hRAGE and hRAGE deletion mutants.

Cells co-transfected with S1-10 hRAGE and S11 hRAGE were viewed by confocal microscopy. The presence of fluorescence demonstrated that RAGE oligomerizes in living cells. Proper expression of each of the RAGE deletion mutants was confirmed by Western blot using anti-T7 antibodies (FIG. 10). Successful construction and expression of RAGE deletion mutants tagged with spGFP S11 provides a means to identify domains within RAGE that are responsible for oligomerization, and will allow for the study of the biological significance of RAGE oligomerization.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A nucleic acid module comprising in the 5' to 3' direction:
   (i) a nucleic acid sequence encoding the signal peptide of receptor for advanced glycation end products (RAGE);
   (ii) a nucleic acid sequence encoding a tag; and
   (iii) a multiple cloning site (MCS), wherein the coding sequence of a heterologous membrane protein is inserted into the MCS.

2. The nucleic acid module of claim 1, wherein the RAGE signal peptide is a human RAGE (hRAGE) signal peptide.

3. The nucleic acid module of claim 2, wherein the signal peptide of RAGE comprises residues 1-23 of SEQ ID NO: 2.

4. The nucleic acid module of claim 1, wherein the tag is an epitope tag.

5. The nucleic acid module of claim 4, wherein the epitope tag is selected from T7, FLAG, HA, VSV-G, V5 and c-myc.

6. The nucleic acid module of claim 1, wherein the tag is an affinity tag.

7. The nucleic acid module of claim 6, wherein the affinity tag is selected from $His_6$, maltose binding protein (MBP), chitin binding protein (CBP) and glutathione-S-transferase (GST).

8. The nucleic acid module of claim 1, wherein the tag is a fluorescent protein.

9. The nucleic acid module of claim 8, wherein the fluorescent protein is a green fluorescent protein (GFP) or a fragment of GFP, wherein the fragment of GFP is selected from the S1-10 fragment or the S11 fragment.

10. A nucleic acid module comprising in the 5' to 3' direction:
    (i) a nucleic acid sequence encoding the signal peptide of receptor for advanced glycation end products (RAGE);
    (ii) a nucleic acid sequence encoding a tag; and
    (iii) a multiple cloning site (MCS), wherein the nucleotide sequence of the nucleic acid module is at least 95% identical to SEQ ID NO: 1 or SEQ ID NO: 3.

11. The nucleic acid module of claim 10, wherein the nucleotide sequence of the nucleic acid module comprises SEQ ID NO: 1 or SEQ ID NO: 3.

12. The nucleic acid module of claim 10, further comprising the coding sequence of a membrane protein inserted into the MCS.

13. The nucleic acid module of claim 12, wherein the membrane protein is a Type I membrane protein or a Type III membrane protein.

14. The nucleic acid module of claim 1, further comprising a nucleic acid sequence encoding a protease cleavage site between the nucleic acid sequence encoding the tag and the MCS.

15. A vector comprising the nucleic acid module of claim 1.

16. The vector of claim 15, further comprising at least one antibiotic resistance gene.

17. An isolated cell comprising the vector of claim 15.

18. A method of expressing a membrane protein, comprising:
(i) cloning the coding sequence of the membrane protein into the MCS of a vector comprising the nucleic acid module of claim 10; and
(ii) transfecting a cell with the vector under conditions sufficient to allow for expression of the membrane protein.

19. A method of detecting oligomerization of a membrane protein comprising:
(i) transfecting a cell with a first vector and a second vector, wherein the first vector comprises (a) a nucleic acid sequence encoding the signal peptide of RAGE, (b) a nucleic acid sequence encoding GFP fragment S11, and (c) a nucleic acid sequencing encoding the membrane protein, and wherein the second vector comprises (a) a nucleic acid sequence encoding the signal peptide of RAGE, (b) a nucleic acid sequence encoding GFP fragment S1-10, and (c) a nucleic acid sequencing encoding the membrane protein, wherein the vectors are transfected under conditions sufficient to allow for expression of the membrane protein; and
(ii) detecting the presence or absence of GFP fluorescence in the cell, wherein the presence of GFP fluorescence indicates that the membrane protein has oligomerized.

20. The nucleic acid module of claim 1, wherein the membrane protein is a Type I membrane protein or a Type III membrane protein.

21. The nucleic acid module of claim 10, further comprising a nucleic acid sequence encoding a protease cleavage site between the nucleic acid sequence encoding the tag and the MCS.

22. A vector comprising the nucleic acid module of claim 10.

23. An isolated cell comprising the vector of claim 22.

24. A method of expressing a membrane protein, comprising transfecting a cell with the vector of claim 22 under conditions sufficient to allow for expression of the membrane protein.

* * * * *